(12) United States Patent
Bridger et al.

(10) Patent No.: US 6,491,647 B1
(45) Date of Patent: Dec. 10, 2002

(54) PHYSIOLOGICAL SENSING DEVICE

(75) Inventors: Keith Bridger, Washington, DC (US);
Arthur V. Cooke, Baltimore, MD (US);
Philip M. Kuhn, Severna Park, MD (US); Joseph J. Lutian, Arnold, MD (US); Edward J. Passaro, Towson, MD (US); John M. Sewell, Cockeysville, MD (US); Terence V. Waskey, Centerville, MD (US); Gregg R. Rubin, Baltimore, MD (US)

(73) Assignee: Active Signal Technologies, Inc., Cockeysville, MD (US)

( * ) Notice: Subject to any disclaimer, the term of this patent is extended or adjusted under 35 U.S.C. 154(b) by 0 days.

(21) Appl. No.: 09/401,762

(22) Filed: Sep. 23, 1999

Related U.S. Application Data

(60) Provisional application No. 60/100,893, filed on Sep. 23, 1998.

(51) Int. Cl.$^7$ .................................................. A61B 5/02
(52) U.S. Cl. ........................ 600/585; 600/500; 128/900
(58) Field of Search ........................ 600/300, 500–508; 128/900

(56) References Cited

U.S. PATENT DOCUMENTS

| | | |
|---|---|---|
| 3,742,937 A | 7/1973 | Manuel et al. |
| 3,807,388 A | 4/1974 | Orr et al. |
| 3,838,684 A | 10/1974 | Manuel et al. |
| 3,926,179 A | 12/1975 | Petzke et al. |
| 4,009,708 A | 3/1977 | Fay, Jr. |
| 4,058,118 A | 11/1977 | Stupay et al. |
| 4,086,916 A | 5/1978 | Freeman et al. |
| 4,120,296 A | 10/1978 | Prinz |
| 4,269,193 A | 5/1981 | Eckerle |
| 4,281,663 A | 8/1981 | Pringle |
| 4,307,727 A | 12/1981 | Haynes |
| 4,331,154 A | 5/1982 | Broadwater et al. |
| 4,406,289 A | 9/1983 | Wesseling et al. |
| 4,409,983 A | 10/1983 | Albert |
| 4,423,738 A | 1/1984 | Newgard |
| 4,561,447 A | 12/1985 | Kawamura et al. |
| 4,784,152 A | 11/1988 | Shinoda et al. |
| 4,799,491 A | 1/1989 | Eckerle |
| 4,802,488 A | 2/1989 | Eckerle |
| 4,807,638 A | 2/1989 | Sramek |
| 4,807,639 A | 2/1989 | Shimizu et al. |
| 4,846,189 A | 7/1989 | Sun |
| 4,867,442 A | 9/1989 | Matthews |
| 4,869,261 A | 9/1989 | Penáz |
| 4,901,733 A | 2/1990 | Kaida et al. |
| 4,938,228 A | 7/1990 | Righter et al. |
| 4,947,855 A | 8/1990 | Yokoe et al. |
| 4,960,128 A | 10/1990 | Gordon et al. |
| 4,987,900 A * | 1/1991 | Eckerle et al. .............. 600/500 |
| 5,033,471 A | 7/1991 | Yokoe et al. |
| 5,101,829 A | 4/1992 | Fujikawa et al. |
| 5,131,400 A | 7/1992 | Harada et al. |
| 5,163,438 A | 11/1992 | Gordon et al. |
| 5,165,416 A | 11/1992 | Shinoda et al. |
| 5,197,489 A | 3/1993 | Conlan |

(List continued on next page.)

FOREIGN PATENT DOCUMENTS

| | | |
|---|---|---|
| EP | 0 443 267 A1 | 8/1991 |
| WO | WO 95/18564 | 7/1995 |
| WO | WO 95/28126 | 10/1995 |

*Primary Examiner*—Kevin Shaver
*Assistant Examiner*—Michael Astorino
(74) *Attorney, Agent, or Firm*—Alan G. Towner, Esq.; Pietragallo, Bosick & Gordon

(57) ABSTRACT

The present invention relates to a non-invasive device for measuring physiological processes. More particularly, it concerns a device that can be applied externally to the body of an animal or human to detect and quantify displacement, force, motion, vibration and acoustic effects resulting from internal biological functions. Specifically, an inexpensive device is disclosed that is compact, light, portable and comfortable, and operates satisfactorily even with imprecise location on the body, ambient noise, motion and light.

93 Claims, 16 Drawing Sheets

U.S. PATENT DOCUMENTS

| | | |
|---|---|---|
| 5,238,000 A | 8/1993 | Niwa |
| 5,243,992 A | 9/1993 | Eckerle et al. |
| 5,269,312 A | 12/1993 | Kawamura et al. |
| 5,284,150 A | 2/1994 | Butterfield et al. |
| 5,406,952 A | 4/1995 | Barnes et al. |
| 5,439,002 A | 8/1995 | Narimatsu et al. |
| 5,467,771 A | 11/1995 | Narimatsu et al. |
| 5,485,848 A | 1/1996 | Jackson et al. |
| 5,490,505 A | 2/1996 | Diab et al. |
| 5,497,779 A | 3/1996 | Takaya et al. |
| 5,509,423 A | 4/1996 | Bryars |
| 5,515,858 A | 5/1996 | Myllymäki |
| 5,551,437 A * | 9/1996 | Lotscher ............... 600/500 |
| 5,617,867 A | 4/1997 | Butterfield et al. |
| 5,622,180 A | 4/1997 | Tammi et al. |
| 5,687,732 A | 11/1997 | Inagaki et al. |
| 5,690,119 A | 11/1997 | Rytky et al. |
| 5,807,267 A * | 9/1998 | Bryars et al. ............ 600/500 |
| 5,908,027 A * | 6/1999 | Butterfield et al. ...... 600/485 |
| 5,921,936 A * | 7/1999 | Inukai et al. ............ 600/485 |
| 5,984,874 A * | 11/1999 | Cerwin .................. 600/485 |
| 6,015,386 A * | 1/2000 | Kensey et al. ........... 600/485 |
| 6,033,370 A * | 3/2000 | Reinbold et al. ........ 600/485 |
| 6,176,831 B1 * | 1/2001 | Voss et al. .............. 600/485 |

* cited by examiner

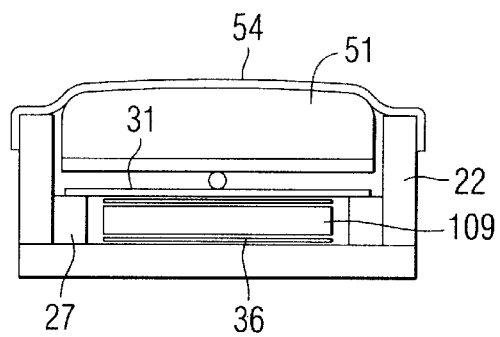
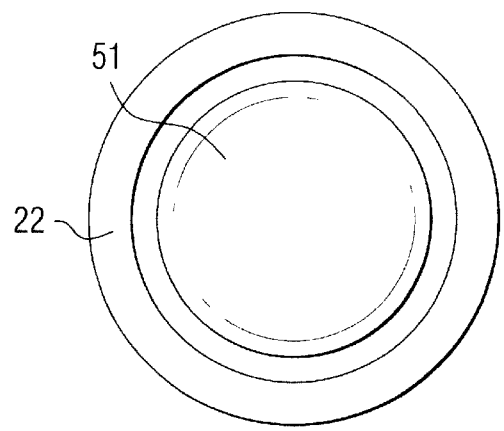
FIG. 13A
FIG. 13B
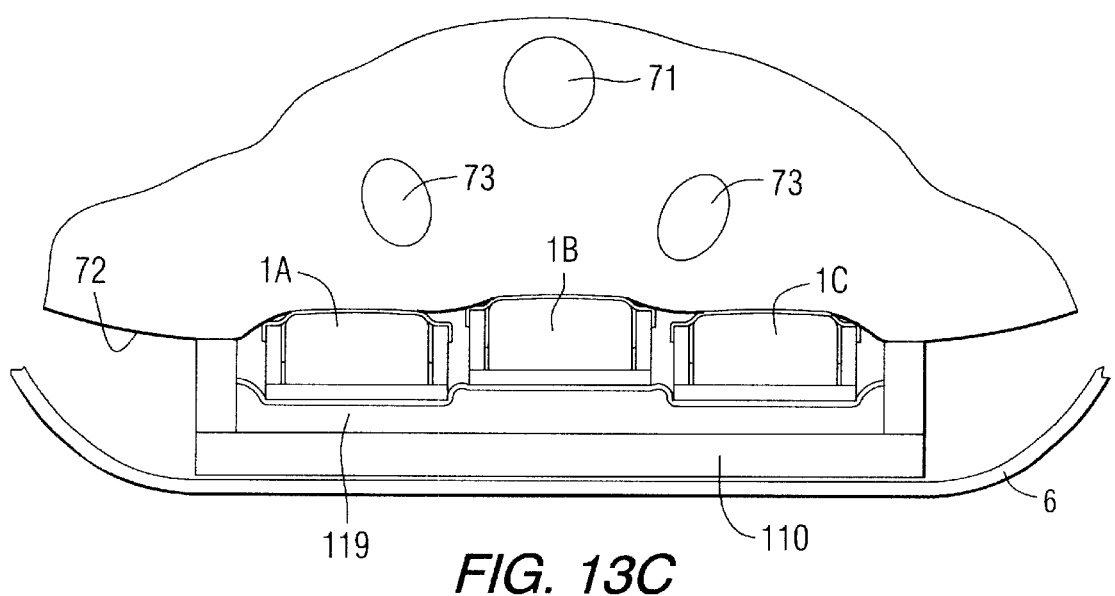
FIG. 13C
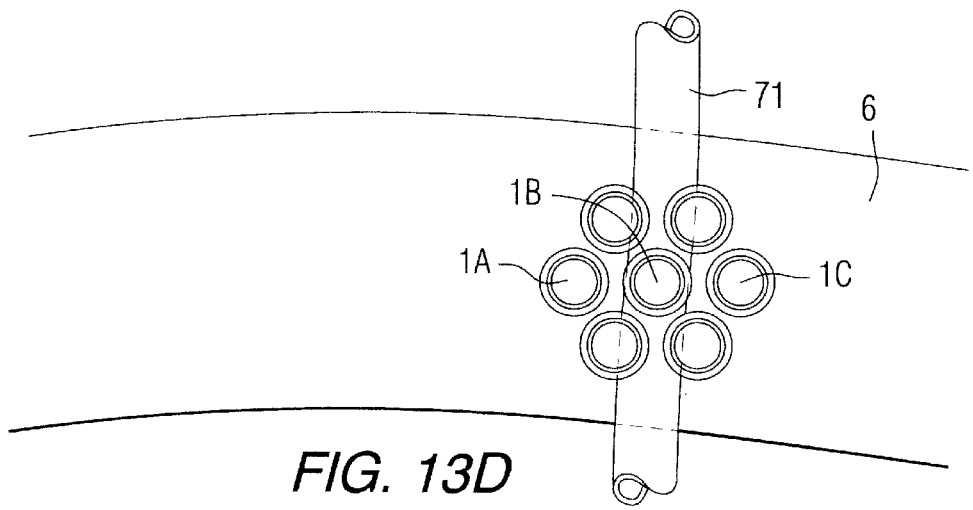
FIG. 13D

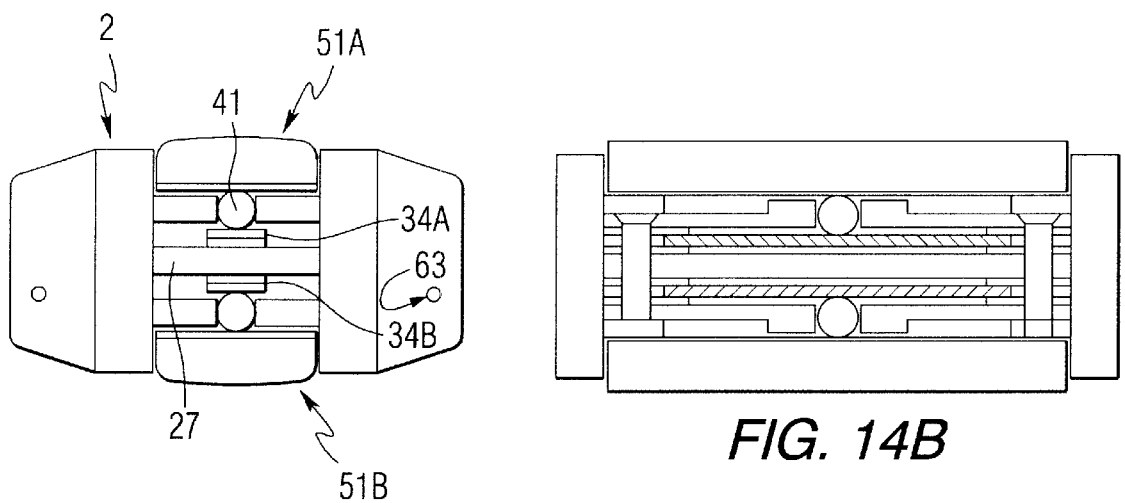
FIG. 14A
FIG. 14B
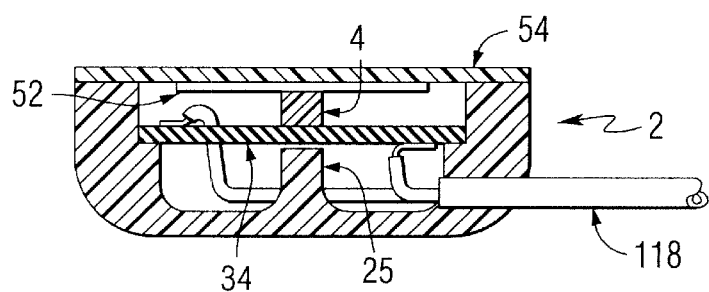
FIG. 15
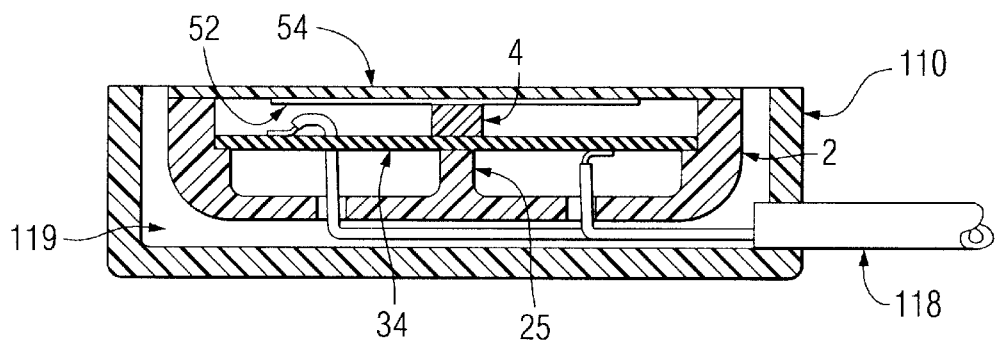
FIG. 16

PHYSIOLOGICAL SENSING DEVICE

CROSS REFERENCE TO RELATED APPLICATION

This application claims the benefit of United States Provisional Application Serial No. 60/100,893, filed Sep. 23, 1998.

FIELD OF THE INVENTION

The present invention relates to a non-invasive device for measuring physiological processes. More particularly, it concerns a device that can be applied externally to the body of an animal or human to detect and quantify displacement, force, motion, vibration and acoustic effects resulting from internal biological functions. Specifically, an inexpensive device is disclosed that is compact, light, portable and comfortable, and operates satisfactorily even with imprecise location on the body, ambient noise, motion and light.

BACKGROUND INFORMATION

Traditionally, non-invasive gauging of physiological processes in vivo has been accomplished either with large, complex and expensive techniques such as X-ray, tomography, magnetic resonance and ultrasound, all of which demand the skills and infrastructure of a medical institution, or with simpler, more portable equipment. In the latter category, devices employing superficially attached electrophysiological electrodes (electrocardiogram (ekg), electroencephalogram (eeg), electromyogram (emg), electrooculogram (eog)) are prevalent, but require skill and surface preparation for proper electrode attachment and cause skin irritation with prolonged use. Small portable "light" devices using optical, ultraviolet and infrared spectroscopic and absorption techniques are also implemented widely based on the availability of miniaturized electromagnetic sources, detectors and support electronics. However, these devices are quite susceptible to interference from movement and/or ingress of ambient light. Motion, displacement, vibration and acoustic sensing techniques have also been developed extensively but have yet to see widespread adoption because their inherent sensitivity to movement, location and noise makes it difficult to interpret signal changes in a normal ambulatory environment. Such techniques range from commercially available, simple, passive actigraphy devices to complex servo-driven systems that react instantaneously to each force or displacement as it is generated by the body. The actigraph is typically a casing attached to the body containing a suspended accelerometer element that responds to all magnitudes and frequencies of motion. During physical activity, it therefore reflects the level of effort being exerted overwhelming any other physiologically derived signals, and during quiet rest periods it becomes sensitive to the body's internal "ballistics" such as breathing, tremor, and heart and arterial pulsation. The servo driven devices are generally invoked to quantify physiological parameters such as blood pressure where the force applied to the actuating element can be used as a measure of the force deriving from the biological function. Typically, these devices are quite bulky, demand external power or compressed air supply and require extensive computation capability. In between these extremes lies a spectrum of devices as described below, covering a range of complexity, accuracy and cost, and varying in effectiveness at combating extraneous signal pick-up. Because of the pre-eminent importance to modern medicine of evaluating cardiovascular function, emphasis has been placed on devices that measure heart rate, arterial pulse profile and blood pressure in the review that follows.

Commercially available devices exist which measure heart rate and provide the output on a wrist-mounted display similar in appearance to a wrist-watch. However, none exist which operate continuously and autonomously without ancillary equipment and without requiring some operation to be performed by the wearer.

Devices with Ancillary Equipment

1. Chest Band Pick-ups

A large number of products are available commercially from manufacturers like Acumen, Bodyguard, Cardiosport, Cateye, Polar, Performance, Sensor Dynamics, Sigma, Sports Instruments and Vetta, which sense the electrical activity of the heart through electrocardiogram type electrodes mounted in an elasticated chest band. The resultant electrical spikes are then identified and transmitted to a display that may be mounted anywhere within the range of the telemetered signal —in a wrist-watch type devise, a bicycle handlebar mounted readout, or a custom computer display on a piece of exercise equipment. However, even on far forward bicycle handlebars the signal can be lost. A typical device is described in U.S. Pat. No. 5,690,119 to Pekka.

While the devices typically provide steady and reliable readings, they are best suited to use for brief periods during exercise rather than as a continuous long-term or all-day monitor. In addition, the readings are affected by other users nearby utilizing similar heart rate monitors, electromagnetic radiation interference, particularly from power lines and motorized equipment. Accordingly, they typically will not work in an automobile, near TV's and computers, and on certain types of exercise equipment using electric motors and video screens. While less constraining than an ear clip or finger stall with their associated wires, the chest band takes time to put on under clothing and is a physical encumbrance to the exerciser. In addition, it typically only functions when good electrical contact is established to the skin, either by moistening with water or through sweat during vigorous exercise. During very vigorous activity such as mountain biking the chest-band will often slip down from the optimum pick-up location.

2. Handlebar Pick-ups

Certain types of exercise equipment, such as treadmills, stair-steppers, etc, are outfitted with electrically conducting handlebars that serve as crude electrocardiogram leads. The change in gross position of the cardiac dipole during the course of each beat is manifest as a measurable shift in surface potential between the right and left side of the body and can be picked up at the gripping surface of each hand.

Although this provides feedback while the exercise equipment is being used, all readings are lost when physical contact with the equipment is broken.

3. Ear Lobe Pick-ups

Some exercise equipment and heart rate monitors come with a small infrared transmitter (a light emitting diode is a typical example) and detector that clips onto the ear-lobe and picks up the fluctuation in IR transmission through the ear as the capillaries fill with blood and then drain during the cardiac cycle. The pulse data is hard-wired from the sensor to a display mounted on the wrist or other convenient location. A typical commercially available product of this type is the Cateye PL-6000.

In addition to being uncomfortable, and awkward (because a wire has to be run from the detector on the ear to a visible display), these devices are prone to interference from movement and changing ambient lighting conditions. The slightest head motion causes changes in the amount of IR radiation detected, hence the apparent pulse rate, due primarily to the light that leaks in around the edges of the detector window.

U.S. Pat. No. 5,490,505 to Diab et al. describes such a device, typically configured as a pulsoximeter on the finger or ear with two different wavelength LED's shining through the tissue to enable an attenuation measurement to be made after propagation through or reflection from the medium. Pulse rate is determined from the periodic attenuation associated with the increase and decrease in arterial flow during a pulse cycle. However the resultant plethysmographic waveform is readily overwhelmed by motion because movement exerts a strong influence on the dynamics of venous blood flow and hence venous blood attenuation of the LED wavelength. Accordingly, the patent describes complex and involved signal processing to recognize the true signal and extract it from exercise-generated noise.

U.S. Pat. No. 4,867,442 to Matthews describes an exercise aid configured as a sweatband around the head with IR or piezoelectric sensors on the ear to pick up pulse. However, the patent provides no enabling disclosure to overcome the motion induced artifacts which would obscure the pulse signal during exercise.

4. Finger Stall and LED Window Pick-ups

While finger stalls are specifically discussed here, the same shortcomings are found with a number of devices used on other parts of the body where there is adequate superficial blood flow, such as the ear, the finger or forehead. Devices requiring fingers or thumbs to be placed over LED windows on the face of a watch are discussed below.

Two devices, the Nissei PU-701 and the Elexis FM-135, are available commercially, which operate on the same principle as the above-described infrared ear-lobe sensors, except that the IR radiation is sent through and received from the fingertip encased in a lightproof finger stall. The resultant information is displayed on a wrist-mounted monitor.

As with the ear-clip, these devices are susceptible to motion and light interference, have external wiring, and are cumbersome and unappealing to wear either during exercise or for routine pulse monitoring during inactive parts of the day. While the lightproof finger stall gives superior results to the LED window types described below, the readings become inaccurate while gripping any object such as a handlebar.

U.S. Pat. No. 4,807,639 to Shimizu describes a watch with either an LED and phototransistor window on its face or a removable finger stall wired to the electronic circuits in the watch case. In either case, a finger is disposed simultaneously over both the LED transmitter and the phototransistor detector (for the finger stall version, both are housed within the stall) such that light reflected by the finger surface, and hence modulated by pulse is detected and counted at the receiving phototransmitter. Because the device only works when the user is motionless and the finger is carefully and properly positioned, the watch is equipped with bar displays corresponding to inadequate readings thereby guiding the user to reposition the finger or move into more favorable ambient lighting conditions.

5. Hand Held Devices

Both ECG type and IR detection type pulse measurements can be accomplished with devices that are held in the hand. One such instrument, the Sportline 390 is held in one hand while the thumb of that hand is placed over an IR window exploiting the same principle as described above for the ear lobe and finger stall sensors. Even though this only occupies one hand, this still constrains most types of activity and the hand must be held very still during a measurement.

Free-standing devices have been developed which operate on the same electrocardiogram principle as the above referenced handlebar pick-ups. In a device made by Pulse Time, the instrument is held in one hand thereby making contact with one electrophysiological electrode and the other hand is brought across to contact an electrically separate part of the device thereby measuring a potential difference across the body during the cardiac cycle. The watches with contact plates described below operate on this same principle. The Biosig Instruments Instapulse series of devices use electrophysiological electrodes embedded in bars and handles that are gripped with both hands. In the Heart Rate 1-2-3E, the thumb of each hand is applied to a different electrode surface on a hand-held unit.

Clearly, these devices are only suitable for intermittent spot checks on pulse because they only work as long as both hands are being used to make the electrical contacts. This is incompatible with exercise and most other types of activity particularly since there is a delay of several seconds after contacting both electrodes before the pulse is displayed.

"Pulse-on-Demand" Devices that Require User Actions or Intervention

1. Watches with LED Windows

Watches have been developed and made commercially available by companies such as Casio and Innovative Time, where the pulse is measured by holding a thumb or fingertip over a small LED mounted in a watch face. The IR from the LED penetrates the superficial capillaries of the finger and the amount of IR reflected back to a co-located detector changes as the volume of blood in the capillaries varies during the course of a pulse.

These instruments have all of the disadvantages common to IR based devices as described above for the finger stall and ear lobe types, such as extreme motion sensitivity, and taking several seconds following application of the finger before a pulse reading is registered. They cannot be used during exercise where hands and arms are involved, and are only useful for occasional discontinuous readings because both hands are needed to take a measurement. In addition, the instructions issued with these watches reflect numerous practical difficulties with the measurement because of sensitivity to ambient lighting conditions, sweat and body hair.

2. Watches with Contact Plates

Working on a similar principle to the above described Handlebar Pick-up pulse monitors, watches have been developed by Seiko, Advanced Body Metrics and Physi Cal Enterprises, for example, which have a small metal plate on the watch face insulated from the metal backing of the watch which rests against the wrist. The user brings across a finger from the opposite hand to touch the insulated metal plate thus setting up the usual two electrode electrocardiogram scheme with one contact as the fingertip and the other, the back of the wrist of the opposite arm.

As with the LED window watch, the device is impractical for continuous reading or measurement during exercise because both hands and arms are tied up by the measurement. In addition, there are electrical contact problems and hence readings become unreliable when the user's wrist under the metal backing of the watch is hairy.

A device of this type is described in U.S. Pat. No. 4,938,228 to Richter where, in the preferred embodiment, the biosignal reflecting the pulse is generated by an electrocardiogram electrode on one wrist and another electrode on the finger of the opposite hand. Other proposed locations included any two well separated parts of the body of opposite polarity. Alternatives to the ECG electrode are microphonic, piezoelectric, photo-optical and capacitive types, but there is no enabling disclosure describing their implementation. In a non-clinical environment, the signal is confounded by movement, low signal to noise in certain individuals, and poor electrical contact to the skin. The patent therefore describes very complex and computationally intensive signal processing and pattern recognition schemes (which incorporate a time-consuming learning cycle before any pulse data can be registered) to overcome these extreme difficulties encountered in trying to extract clean pulse data from non-medical, non-chest mounted ECG leads. After applying the computational methods of the invention, 50% of subjects still gave unsatisfactory readings during exercise, suggesting the need to slow or stop the exercise or abrade or wet the skin.

Self-contained Devices on the Wrist

The above-described shortcomings of wrist pulse displays which require ancillary equipment or which require manual intervention, have spawned a large number of attempts to develop a device that is continuous reading, autonomous and fully self-contained on the wrist. While many have been invented and patented, none have been successfully developed into commercially viable products. Some of the more promising attempts and their shortcomings are reviewed below.

1. Pressure/Displacement Sensors

In U.S. Pat. No. 3,807,388 to Orr, a heartbeat rate monitor or personal pulse indicator is described employing a sensor that is either a "pressure sensitive resistor" or a "pressure sensitive transistor". Beyond these generic terms, no further description is provided for implementing these sensor types to ensure high signal to noise, to avoid signal loss with wrist movement or to adapt to a wide range of input signal strengths. For either sensor type, the sensing element is shown embedded in, and protruding from, the inner surface of a wrist strap to react to pressure changes at the surface of the wrist during the course of a pulse. To counter random movement of the strap, the sensor is held firmly in one position on the wrist and not allowed to slide by virtue of a stabilizing frame that also protrudes from the strap beyond the circumference of the sensor element. The sensor elements shown to be very small in comparison to the width of the strap, and from the figures, measures approximately $\frac{1}{10}$ inch in diameter.

In U.S. Pat. No. 4,120,296 to Printz, a pulsimeter is described for indicating the average heart beat rate using a sensor adapted for flat application against the body, preferably at the wrist. The device merely uses a commercially available sensor, known as a Hewlett Packard digital plethysmograph model 14301A. From the drawings and method of application, the sensor appears to be about $\frac{3}{8}$" in diameter and thin enough to completely embed in a conventional watch-band (<$\frac{1}{10}$"). There is no discussion of modification to the sensor or its implementation to improve signal to noise ratio, compensate for location specificity or to accommodate a wide range of input signal strengths.

In U.S. Pat. No. 4,009,708 to Fay, a pulse recorder is described, self-contained in a wristwatch type case. The sensor is either a microphone or a pressure sensor, approximately $\frac{1}{4}$–$\frac{3}{8}$" in diameter as shown in the figures, but no further description or implementation is provided to explain how practical issues are resolved, such as location sensitivity, signal strength changes and competition with noise signals. Moreover, the sensor forms part of the back face of the case and therefore bears on the upper surface of the wrist where there is very little acoustic or pressure activity occasioned by the pulse.

In U.S. Pat. No. 3,742,937 to Manuel, a self-contained, compact cardiac monitor is described for strapping on the wrist over the region where the radial pulse is normally detected. Two sensor mechanisms are described, both using a differential pressure detector scheme within a chamber of encapsulated low viscosity oil. The outer surface of the sensor is constructed of pliable silicone rubber which moves in response to the pulse and thereby displaces silicone oil in a centrally located pocket. In one case, a thin leaky silicon diaphragm with embedded strain gauges divides the encapsulated oil into two chambers. During the course of a pulse, the oil moves and deflects the diaphragm producing a measurable signal on the strain gauges. In the other case, the oil is divided into two sub-chambers by the flexible central conductor plate of a capacitor so that the capacitance of the circuit changes in response to oil movement during a heart beat. Overall dimensions of the silicone rubber enclosure are $\frac{1}{4}$–$\frac{1}{2}$" in diameter and 0.1–0.2" thick.

In U.S. Pat. No. 4,281,663 to Pringle, a physical fitness indicator is described utilizing a piezoelectric displacement sensor similar to a crystal phonograph pick-up attached to the wrist, throat or ear lobe. Although Pringle states that it is technologically feasible to house the whole device in a watch-type case with the sensor bearing on the radial pulse, no description of the sensor is provided, nor is there any discussion of how to overcome location sensitivity and motion artifacts. In addition, while the signal conditioning electronics and processing software identify and count pulses, no consideration is given to managing input signals with vastly differing magnitudes and signal to noise ratios.

In U.S. Pat. Nos. 4,331,154 to Broadwater and 4,307,727 to Haynes, a self contained wrist-mounted blood pressure monitoring system is described employing a very small diameter rod digging into the skin above the radial artery. The rod has a tiny piezoelectric crystal mounted on the end that engages with the skin to respond to the displacement pulse as a bolus of blood passes down the vessel. No attempt has been made to match the impedance of the hard ceramic crystal on top of the hard rod to the mechanical impedance of the physiology. A simple tensioning mechanism adjusts the length of the wrist band until the artery is flattened to half its initial diameter. In fact, it is likely that most of the motion produced by pulsation in the artery would be taken up in compliance of the band and mechanisms behind the piezoelectric crystal rather than getting coupled into the crystal itself.

2. Ultrasonic Devices

In U.S. Pat. No. 4,086,916, a cardiac monitor wristwatch is described with an ultrasonic transmitter and receiver in the wristband. The device registers movement of the outer surface of the radial artery by frequency difference between the impinging and reflected signals as the artery expands and contracts during a heartbeat. While the ultrasonic transmitter is power consuming and would therefore not appear suitable for continuous monitoring with a typical small watch battery power supply, it is claimed that the existing watch battery will suffice because the transducers are very directional and therefore efficient.

Non-invasive Non-occlusive Blood Pressure Measurement Devices

While numerous methods have been proposed for continuously and non-invasively measuring blood pressure as an alternative to the invasive arterial line, none have yet reached the point of widespread medical acceptance and commercial availability.

In the standard arterial line technique, a pressure sensor is inserted into the artery or into a contained volume of blood in free communication with the artery, and generates a signal that continuously and accurately reflects the blood pressure. However, the procedure is uncomfortable, expensive, consumes care-provider time and risks embolization, nerve damage, infection, bleeding and vessel wall damage.

The standard non-invasive device is the automatically inflating pressure cuff (applied over either the brachial or the radial artery), which can be uncomfortable with repeated use and only provides discontinuous sample readings at the time the device activates. The device typically requires 15–45 seconds to take a reading and, because it is occlusive, a minimum of 15 seconds must be allowed between readings to allow sufficient venous recovery. Also, frequent cuff inflations can produce ecchymosis and nerve damage under the cuff after extended periods of use. The oscillometric signal utilized by a cuff is also very sensitive to motion of the arm.

Another commercially available non-invasive blood pressure measuring device is the Finapres which employs photoplethysmography, e.g., as disclosed in U.S. Pat. No. 4,846,189 to Sun, U.S. Pat. No. 4,869,261 to Penaz and U.S. Pat. No. 4,406,289 to Wesseling, to interrogate the diameter of a blood vessel and correlate this to pressure. A small cuff containing an IR source and detector tuned to the wavelength for hemoglobin is inflated around a patient's digit. After measuring the mean arterial pressure, from then on, the device adjusts the applied pressure to maintain the diameter of the artery constant (transmural pressure held at zero). As the patient's blood pressure changes, this is then reflected in a change in the pressure that must be applied to hold the diameter of the artery fixed. This device has been found clinically unsatisfactory because changes in arterial diameter due to changes in arterial wall compliance (vasomotor tone) are falsely registered as blood pressure changes. In addition, the constant pressure is uncomfortable over extended periods of monitoring, and the peripheral blood pressure measured in a finger is not necessarily representative of central blood pressure, particularly if the vascular circulation is poor or there is peripheral vasoconstriction.

In U.S. Pat. No. 5,406,952 to Barnes, a wrist mounted device is disclosed for non-invasively measuring blood pressure, comprising a pressure/displacement pick-up with a piezoelectric sensing element mounted over the radial artery on the underside of the wrist. The piezoelectric element is a unimorph disk constructed from a 10 mil brass substrate with a 10 mil layer of piezoelectric ceramic deposited on its surface. The element is activated by a small diameter rod protruding from the device into the skin above the radial artery at one end and bearing on the center of the disk at its other end. The disk is suspended from a compliant circumferential ring of silicone rubber which diminishes the amount of energy transferred into the electroactive element. In principle, as a bolus of blood passes along the radial artery during a pulse, the artery expands, raising the skin and flesh above it and displacing the rod into the piezoelectric element. In practice, it would be very difficult to assure accurate and reliable positioning of the small diameter rod over the radial artery, particularly in view of lateral displacement of the radial artery as the wrist is rotated and repositioned. Accordingly, there would be an unacceptable amount of signal attenuation and even complete drop-out accompanying normal movement. To counteract this position-dependent effect and prevent motion artifact as the rod gets pulled against the skin, patentee uses an adhesive foam interface to hold the actuating rod exactly in place. However, the band used to keep the device on the wrist does not run over the sensor housing and therefore does not apply pressure to help keep the housing in mechanical contact with the wrist. In addition, the signal levels from this device would be extremely low and hence difficult to extract from noise because the unimorph disk configuration is relatively stiff and very little force is applied to it by the rod because of the small area of contact between the externally protruding end of the rod and the artery wall which provides the driving force. Another way of considering this is that the actuating rod is fairly difficult to move into and out of the plane of the disk and therefore is effective at resisting the motion of the artery wall. Accordingly, the flesh and skin expansion during each pulse will tend to "side-step" the rod and instead expand into the neighboring tissue. To derive a blood pressure from the displacement signal, patentee uses a signal processing scheme that is totally independent of signal amplitude and instead relies on an empirically derived set of correlation factors applied to their pattern recognition and morphology analysis.

In U.S. Pat. No. 5,485,848 to Jackson, a non-invasive, non-intrusive, convenient and portable blood pressure measuring device is described based on sensing the user's arterial wall movement. Although no details or implementation are provided, it is suggested that the sensing can be accomplished with an aneroid chamber, strain gage, optical motion sensor or hydraulic sensor. Absent such details, it is not clear how the devices would be applied to overcome signal to noise problems, widely disparate input signal levels and signal attenuation with position changes. The one sensor implementation that is described, utilizes a film of piezoelectric polymer embedded in the inner surface of a wrist band. Much attention is given to band tensioning and locking mechanisms in addition to automatically controlled motorized tension adjusters. Even with these measures, it likely that the signal to noise ratio would be inadequate for pulse measurement with this device, particularly as the signal became obscured by movement and other extraneous phenomena.

In U.S. Pat. Nos. 4,960,128 and 5,163,438 to Gordon, a film of piezoelectric Kynar is disposed over the artery to sense the pulse and transmit the signal over a 10 foot cable to a signal processing means. Because the film has inherently poor electromechanical coupling and is applied directly to the skin without any modification to match its mechanical impedance to the physiology under test, the example pulse trace is very noisy and must be integrated to smooth the curve and eliminate noise. Blood pressure is obtained by feeding the Kynar signal into a standard arterial line monitor after applying a correction factor to the signal amplitude. The correction factor is an empirical scaling value that depends on how much of a frequency shift there is between the frequency corresponding to the maximum amplitude (based on a Fourier transform) of the pulse in question and the initial calibration pulse. Signal processing is applied. There is no provision for motion or other noise compensation, or means to handle a wide dynamic range of input signal amplitudes.

In PCT Pat. No. WO 95/18564 to Kaspari, a piezoelectic film is disposed over the artery in question together with two outside elements whose output is summed and subtracted from the main sensor to minimize sensitivity to motion artifact. Blood pressure is determined by breaking down the measured pulse profile into all of its components (both phase and amplitude) related to different physiological functions and identifying those that correlate best with changes in blood pressure. Pattern recognition and neural networks are used to "learn" which features provide the best match to blood pressure during a "training" phase on the patient. These features and empirical relationships are constantly updated based on calibration values from a non-invasive cuff. To shorten the training process, a historical database is developed on a large population of patients where blood pressure is measured continuously and invasively via catheter and compared side by side with the non-invasive piezoelectric signal to predetermine which features correspond best with blood pressure.

In U.S. Pat. No. 3,926,179 to Petzke, a tonometer is described comprising a bulky apparatus resembling a long thick rod applied orthogonal to the wrist above the radial artery. The rod is not suitable to be self-contained on the wrist because it incorporates a power-consuming servo-controlled pressure applying means to compress the artery to half its thickness and thereby maximize the signal strength and eliminate artifacts due to circumferential components of the arterial expansion. The sensor mechanism positioned at the center of the pressure applying piston is smaller in diameter than the artery under interrogation and comprises a flexible resilient diaphragm with a few tiny elements on its surface that expand and contract as the diaphragm flexes in response to the pulse. Since the electrical resistance of the elements changes as they are mechanically strained, a differential resistance between centrally and peripherally disposed elements provides a measure of the pulse amplitude. Because the sensor is so small, it would have to be very accurately placed and held in position, and the signal strength would be very susceptible to arm movement or rotation. No provision is made for rejecting motion artifacts.

Other tonometric devices are described in U.S. Pat. Nos. 4,269,193, 4,799,491 and 4,802,488 to Eckerle, U.S. Pat. No. 4,423,738 to Newgard, U.S. Pat. No. 5,033,471 to Yokoe, and U.S. Pat. No. 5,165,416 to Shinoda, and a commercial implementation is available through Colin Medical. This device uses a multielement piezoresistive sensor to pick up the amplitude of the pulse at the wrist and use this to follow blood pressure trends between oscillometric cuff readings. The sensing element is small compared to the artery and so will give readings that are very location dependent as the patient moves.

Another non-invasive technique uses pulse transit time (typically to the ear lobe and to the finger) to correlate with blood pressure, as disclosed in European Patent 0 443 267 A1 to Smith. The arrival time of the pulse at the ear and finger is measured by photoplethysmography at each location and used to calculate a change from the calibration pressure measured with a cuff. However, the technique does not compensate for changes in shape of waveform, and even small movements and noise cause relatively large errors in the delay time because the transit times are very short along major arteries.

PCT WO 95/28126 to Caro describes an active interrogation scheme for determining blood pressure by measurement of pulse wave velocity down the arm, whereby a small amplitude excitation signal (20–600 Hz) is superimposed onto the normal pulse profile using air pressure modulation in a cuff inflated on the forearm near the elbow. The combined pulse and superposed perturbation are received by a piezoelectric film over the radial artery and the resultant signal processed by analysis of phase relationships to separate out the three constituents—the pulse, the perturbation and noise. Pattern recognition is used to ensure that a true pulse has been received. Blood pressure is determined from look-up tables based on both the velocity and phase of the superposed exciter wave. Values in the tables derive from statistical measurements taken on a representative population of patients. The piezoelectric receiving sensor is held in place with a second pneumatic cuff that also acts as a baffle to keep out external noise. A third pneumatic cuff is applied over the biceps in conventional fashion to measure a calibrating oscillometric blood pressure. In one alternative embodiment, the need for a calibration cuff is eliminated by including a second excitation signal on the pulse carrier wave. In another, the exciter and sensor are both located over the wrist. However, the device is not suitable to be self-contained on the wrist because of the computationally intensive signal processing and the need for bulky and power consuming inflation cuffs and regulators.

In U.S. Pat. No. 4,807,638, electrical bioimpedance measurements are made between two segments of body tissue to determine the pulse wave velocity.

Many previously described attempts to gage pulse and blood pressure rely on direct contact between a sensing element and the skin above an artery. While new classes of extremely pressure sensitive materials and devices are now available in forms that can readily be miniaturized to the configuration of an unobtrusive wrist sensor, none of these can meet the very exacting requirements of a wrist-mounted pulse sensor without significant modification, and incorporation into systems which accommodate the physiological variables and the motion and noise environment. Examples of these materials and devices include the elastomeric sheet material polyvinylidene difluoride (PVDF), semiconductor strain gages, pressure sensitive resistors and diodes (and their semiconducting counterparts), and piezoelectric crystals and composites. Many attempts have been made to sense pulse by interfacing these materials and devices directly to the body at locations such as the neck, forehead, wrist and thigh where arteries lie close to the surface of the skin. The following patents provide a good range of examples where the material or device is placed directly against the body at the point above the artery, either alone or as the outer surface of a contact pad in a more elaborate application mechanism—U.S. Pat. Nos. 4,784,152; 4,901,733; 4,947, 855; 5,101,829; 5,131,400; 5,238,000; 5,439,002; 5,467, 771; 5,497,779; 5,551,437; 5,515,858; and 5,509,423. In all cases, even though the sensing element is very sensitive, the pulse pressure wave manifest at the body surface is so subtle that the target signal is readily lost in or confused with noise and other environmental influences.

While some inventors have recognized the benefit of capturing arterial displacement signals over a broad area on the surface of the body and have provided relatively large contact pads to accomplish this end, these pads usually contain sensing elements in the contacting surface and therefore do not work satisfactorily for the reasons given in the preceding paragraph. However, the present invention preferably employs an inert (non-sensing) contact pad that acts through a mechanical load capture and transfer element which in turn activates the sensitive material or device. The inert pad responds to a displacement at any point on its surface and focuses the energy onto the sweet spot of the sensor. The prior art techniques introduce complexity into the system by attempting to achieve wide area pick-up by populating the contacting surface area of the pad itself with actual sensing elements. Any energy incident on the contacting surface area at a point not populated by a sensor is not detected by the device. An additional problem, as will be described below, is that this direct interfacing technique does not provide enough separation of the signal from the noise. In addition, new layers of computation and optimization are required to continually select the sensor with the best signal and/or weight inputs from the different sensors.

To avoid the above referenced problem of low absolute sensitivity to the pulse wave and high susceptibility to noise with techniques and devices that use direct contact sensing, techniques have been proposed that separate the two functions of contacting the body surface and sensing the displacement. For example, in U.S. Pat. No. 3,838,684, surface contact is effected with a fluid filled elastomeric bladder while the arterial motion signal is picked up remotely in the fluid through distortion of a central baffle plate which in turn actuates a capacitative displacement sensor or strain gages located on the plate. In U.S. Pat. Nos. 4,058,118, 4,409,983 and 4,561,447, the pulse is initially interfaced with a contact pad which then transmits the load to the center of a small beam with a strain gage or a beam of piezoelectric material, either crystalline, bimorphic or configured as a bender bar. While this arrangement is used in 4,058,118 to transfer pressure received over a gently contoured area of contact pad onto the center of a piezoelectric element, the pad is constrained to move only along the axis perpendicular to the plane of the piezoelectric crystal because it can only move within the fixed geometry of a piston and cylinder type arrangement. Automatic gain control circuiting on the signal input is employed, but the patent does not address signal susceptibility to mispositioning and motion. Accordingly, it is recognized that the device alone cannot combat the problem of noise and motion infiltration hence requiring that the device only be used during very quiet, stationary periods.

In U.S. Pat. Nos. 4,409,983 and 4,561,447, the same basic mechanism is used as above in U.S. Pat. No. 4,058,118, but soft cushioning material or springs are incorporated into the outer mounts for the piezoelectric or strain gage beam to dampen the structure and mechanically filter out high frequency noise. While patentees claim the resultant motion and noise pick-up are significantly diminished, the soft mounting feature greatly reduces the absolute sensitivity of the piezoelectric beam sensor. Because there is such a huge variation in arterial pulse signal strength, associated with individual differences, changes during the day, changes with limb position, changes with health and exercise, etc., the greatest possible absolute sensitivity of the sensing element is required to ensure that the entire dynamic range can be covered.

In Pat. No. 4,561,447, a single element sensor embodiment of the invention is described which is designed to be hand-held against the neck of a patient by a caregiver who can properly place the device over the carotid artery by lining up the cut-outs in either end of the sensor. Exact positioning is critical because of the particular actuating mechanism, where a presser portion is used to contact the body over an artery and an abutment portion transfers the load onto the center of a flexible beam incorporating a strain gage, mounted at its ends. The size of the presser portion is less than the diameter of the artery under interrogation since the presser portion fits within end slots (cut-outs) in the housing designed to accommodate the projection of the artery at the surface of the body. In addition, the direct spatial relationship of the presser and abutment creates inherent sensitivity to getting mis-positioned because it ensures that only those forces or displacements impinging directly on the relatively small area of presser surface are transferred to the measuring strain gage. This point is emphasized in the disclosure of two multi-element embodiments of the invention developed for the purpose of overcoming distortion associated with the sensor getting displaced in any way from its optimal position on the body. In one of these embodiments, the line of elements traverses the artery, thereby allowing one of the plural presser portions to be located within an area of the neck skin in which the pulse wave of the carotid artery can be detected as a sufficiently high level of electric signals without a distortion. In the other embodiment, the plural sensors allow detection of a pulse wave signal without a distortion which could be caused by misalignment of a detector or sensing device relative to the carotid artery when the detector has a single sensing unit.

The 4,561,447 patent also places great weight on high fidelity replication of the exact pulse profile and defines a distortion parameter that has to be kept below a certain level to satisfactorily meet the requirements of the invention. The principal factor controlling distortion is the depression pressure experienced at the actual sensing surface against the body. Accordingly, a highly compliant (elastic modulus as low as practicable) mounting material (foam, elastomer, springs, etc.) is introduced under the end-mounts of the sensing beam to ensure that the depression pressure remains within the optimal range while the actual application force from the user's hand varies widely from very light to very strong application. When a high modulus mounting material is used, the depression pressure becomes too high, causing the pulse wave signal to be distorted.

The present invention has been developed in view of the foregoing, and to address the deficiencies of the prior art.

BRIEF SUMMARY OF THE INVENTION

The invention described below is intended to provide a simple, inexpensive, compact and portable device for sensing physiological signals while overcoming the prior art difficulties of susceptibility to noise, motion, orientation (attitude of body member to which the sensor is attached) and inadequate dynamic range to cover the broad spectrum of actual input signals encountered in physiological measurements. To reduce the response of the device to force and acceleration associated with gross body movement, the sensing element, coupling mechanism, and its mounting structure are made extremely light and are all tightly coupled to the body surface at the point of attachment such that both the element and its mount receive the external motion equally and can therefore cancel it as a common mode in a difference measurement. Depending on the demands of the specific application, noise and motion effects are optionally further reduced through subtraction and filtering schemes based on the frequency content detected in a separate optional motion sensitive element or elements, common mode rejection employing another comparable optional sensor, or sensors, located away from the maximum physiological signal, or signal processing to extract recognizable physiological signal patterns from noise and motion artifact. Advanced detection and tracking electronics are used to span the very demanding dynamic range of sensitivity needed to follow signals as they vary widely from individual to individual, and within an individual with level of physical activity, time of day, state of health, limb orientation, etc. The dynamic range is also maximized through use of an extremely sensitive sensing member, firmly mounted with respect to the sensor housing and actuated with considerable mechanical advantage by the physiological process at a very sensitive point on the sensing member. Mechanical advantage is achieved by not placing the sensing member in the contact face of the device so that it can be actuated by a pressure amplification mechanism. Problems with loss, or decreased amplitude, of signal with misalignment from the ideal sensing location are minimized with a novel design of "free-floating" contact pad that interfaces to the body over an area that is broad enough to encompass most of the area of the body where effects of the physiological process in question are manifest. This interface not only conforms comfortably to the contour of the skin but responds in an essentially omnidirectional fashion to forces and displacements incident at any angle onto the outer face of the pad. While the pad is simply an inert mechanical collector of force and displacement, it couples via a mechanical transfer mechanism to a highly sensitive portion of a sensing member. Optionally, to ensure that device responds to the physiological process but not to unrelated noise or motion, the mechanical transfer mechanism is constrained to respond only in one axis directed towards the source of the physiological phenomenon and thereby reject any motions or forces the contact pad has picked-up in orientations away from this axis.

A specific use of the invention is as a non-invasive device for use on mammals including humans and other animals to sense blood vessel wall motion and blood vessel wall position, measure pulse rate and/or amplitude and shape of arterial pulse profile from which to derive blood pressure. The sensor and conditioning electronics of the device are also suitable for measuring parameters such as vascular wall compliance, ventricular contractions, vascular resistance, fluid volume, cardiac output, myocardial contractility and other related parameters.

To be configured for continuous use as a cardiovascular monitor, the sensor assembly is preferably made as light and compact as possible and applied with a band over a suitable artery on the body. Preferably, the device is made fully self-sufficient with sensor assembly, support electronics, power supply, processing and display all incorporated on the same band.

In a preferred embodiment, the device is non-encumbering and suitable to be worn continuously and to calculate and readout pulse and blood pressure continuously or as required. The device is sensitive to pressure/displacement signals of widely varying magnitude collected over a broad area on the underside of the wrist, and includes signal conditioning electronics that automatically normalize the signal level to facilitate digital processing and counting. Optional data storage and digital interfaces, such as a standard RS232 port or infrared communications link, may also be included to increase the versatility, appeal and usefulness of the device. For this embodiment as a wrist worn pulse counter, it is an aspect of the present invention to provide the following combination of features: no ancillary equipment (such as chest band, ear lobe clip, finger stall, equipment to hold, window or plate to touch) beyond the self-contained wrist device itself; convenient all-day comfort and portability, wearability; continuous ongoing measurement and display; no action or intervention required of the user to activate readings; insensitive to hair, sunlight, sweat; and cleanest possible sensor signal with highest fidelity replication of the motion of the arterial wall movement to minimize or eliminate the need for complex signal processing techniques, learning and pattern recognition.

These and other aspects of the invention will be more apparent from the following description.

BRIEF DESCRIPTION OF THE DRAWINGS

FIGS. 13A–D depict a preferred embodiment of the present invention wherein the sensing device is made very small, enabling multiple devices to be deployed across an area of the body.

FIGS. 14A–B depicts a sensor in accordance with the present invention with an equivalent opposite facing sensor for noise and motion cancellation purposes.

FIG. 15 is a sensor in accordance with the present invention used for sensing acoustic phenomena without an outer contact member.

FIG. 16 is an acoustic sensing device in accordance with the present invention with passive isolation means to exclude externally imposed artifact and noise

DETAILED DESCRIPTION OF THE INVENTION

Figure 1:
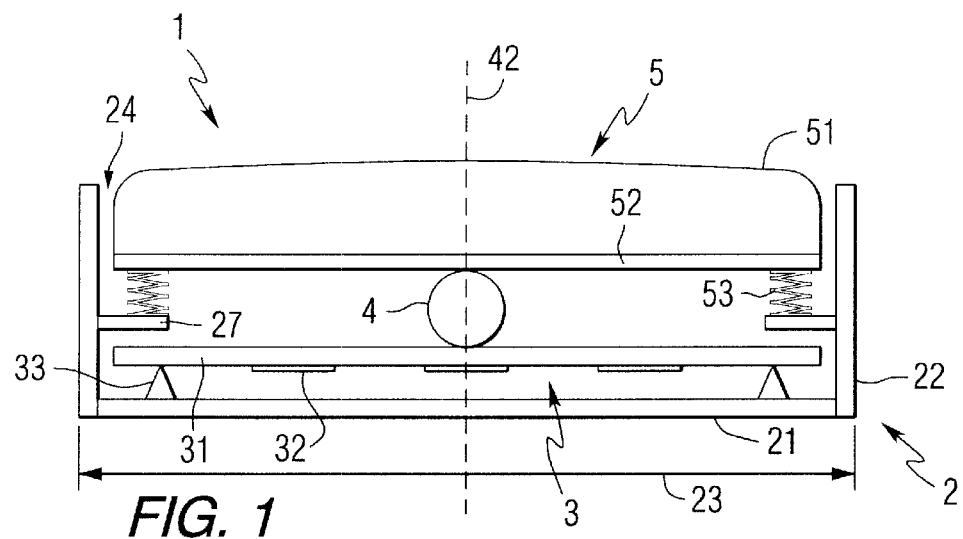
FIG. 1 shows a schematic cross-section through a non-invasive sensing device in accordance with an embodiment of the present invention.

FIG. 1 illustrates a preferred embodiment of the physiological sensing device 1 of the present invention wherein one or more sensing elements 32 are contained in a rigid or semi-rigid housing 2, which may be enclosed on two or more sides 22. The housing 2 comprises a protective mounting enclosure made of plastic, composite, rubber, metal or other light material with side-walls 22 defining an opening 24 at one end. The opposite end of said housing may optionally be enclosed using a base 21. An interface transition mechanism 5 is defined by outer contact member 51, stiffening member 52, and compliant return elements 53. Construction material and contour of outer contact member 51 are designed for conformity and compatibility with surface under interrogation. A stiffening member 52, shown as a thin metallic sheet, ensures that all forces and displacements incident on outward facing surface of the outer contact member 51, shown as a molded plastic form, are transmitted efficiently to a load transfer element 4. Although physiologically derived forces are all collected through their effect on the outer contact member 51, said outer contact member does not contain sensing elements in its surface facing the physiological source. Compliant return elements, shown as elastomeric pads resting on structural or spacer blocks 27, maintain initial orientation and position of the outer contact member 51 relative to the housing 2 prior to applying to a physiological source, while allowing easy reorientation to match local anatomical contour when applied to the source while still maintaining gross position. Accordingly, the outer contact member 51 is very loosely mounted, or essentially free floating, and over the geometric limits of linear travel towards and away from the base 21, can rotate freely about its contact area with the load transfer element 4. The rotation is typically about axes lying in the plane normal to the sensing axis 42.

An interface transition mechanism 5 contacts the load transfer element 4, shown as a hard spherical contacter, which in turn contacts a sensing portion 3. The components are mechanically arranged to enable forces incident at almost any angle on outer surface of the outer contact member 51 to be transmitted effectively to the most sensitive region of the sensing portion 3. The load transfer element 4 may be configured in any suitable form, such as a sphere, a rod with rounded ends contacting interface transition mechanism and sensing portion, respectively, or a rod whose axis is perpendicular to the sensing axis 42 and perpendicular to the length dimension 23. The load transfer element 4 is typically rigid or semi-rigid and may be constructed from plastic, rubber, metal or other light material. For different applications, the load transfer mechanism 4 may contact the interface transition mechanism 5 and the sensing portion 3 at a point or along a line to facilitate rotation, or may be attached at either or both ends, or may be provided with joints such as ball and socket joints at either or both ends. A signal is measured when the load transfer member transmits forces to the sensing portion 3. It should be noted that sensing portion 3 is remote from the body surface 72 and only receives forces after mechanical transmission through the mechanism of the present invention.

For many applications, it is critical to minimize the overall height of the device 1 from the outer contact member 51 to the base 21. This is accomplished by suitable design of the sensing portion through selection of construction and sensing materials and design of mounting schemes and mechanisms. The combined effect of mechanical design and selected sensing elements must be to produce readily measured signals at extremely small displacements along the sensing axis 42.

In a preferred embodiment shown in FIG. 1, the sensing portion 3 is constructed from a displacement member 31, sensing elements 32 and support mechanism 33. The displacement member 31 is capable of deflecting by an amount readily detected by the sensing elements 32 in response to forces transmitted from the interface transition mechanism 5 through the load transfer element 4. The support mechanism 33, shown as pivot points or knife edges towards the end of beam 31, is designed to present maximum deflection or force, as appropriate, at the most sensitive portion of the sensing elements 32, illustrated in FIG. 1 as strain gages. The sensing portion 3 may comprise any of a variety of materials or mechanisms that are sensitive to pressure, displacement and force, such as solid state or optical fiber pressure sensors, piezoelectric, electrostrictive and magnetostrictive materials, and proximity sensing devices based on capacitative, eddy current, optical, magnetic and inductive phenomena.

Figure 2:
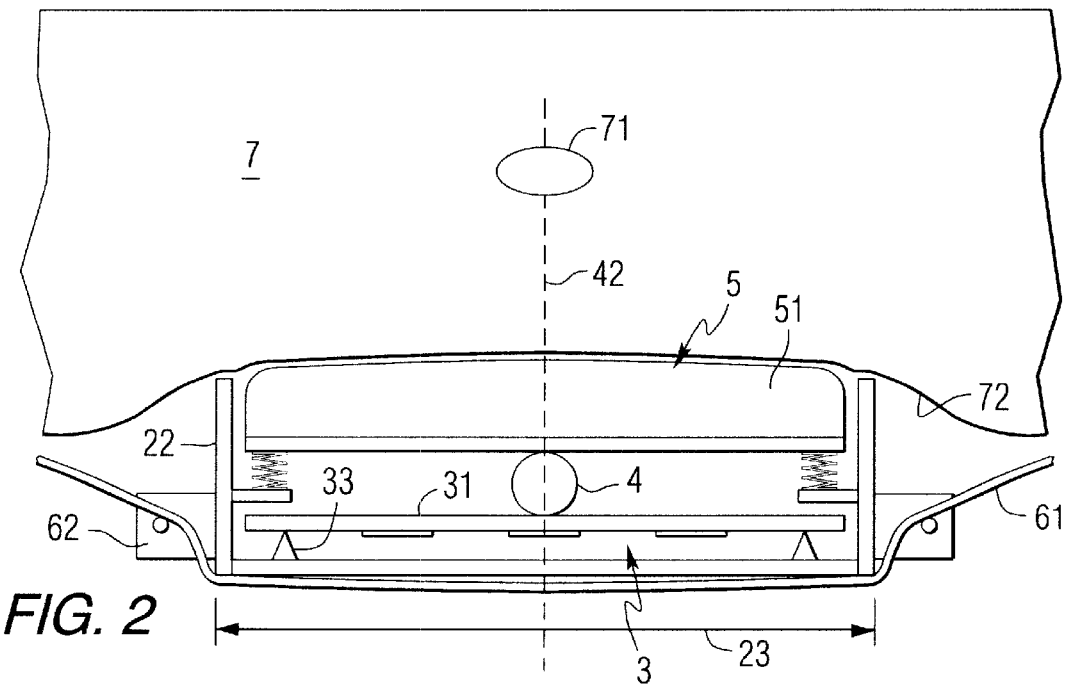
FIG. 2 shows a schematic cross-section through a non-invasive sensing device in accordance with an embodiment of the present invention, illustrating its application using a strap or adhesive tape to a portion of a body adjacent a source of physiological signals.

FIG. 2 shows a physiological sensing device 1 of the present invention mounted against an outer surface 72 of a human or animal body 7 and held in place with attachment means 6 comprising a strap 61 and tabs 62. Tension of the strap 61 is adjusted to provide a comfortable wearing pressure of the device 1 against the body 7 and ensure intimate interfacial contact. The length or tension adjustment on the strap 61 is preferably performed just once by the wearer for initial fitting, locked at this setting and then released and reapplied on future occasions with a snap, clip, hook or other quick release mechanism. The outer contact member 51 is centered approximately over the area of the body surface 72 where the displacement or force deriving from a physiological source 71 is manifest. The displacement or force is effectively transmitted via the outer contact member 51, stiffening member 52, load transfer element 4 and displacement member 31 onto the sensing elements 32. Forces impinging diffusely over a range of angles to the surface and over a relatively wide area on outer contact member 51 are concentrated on the small contact area between load transfer element 4 and sensing portion 3, and the primary force component transmitted is along the sensing axis 42, normal to the displacement member 31 and lying between the physiological source 71 and the load transfer element 4. Accordingly, even a low force manifest over a wide area at the body surface 72 at an angle that is not normal to the sensing axis 42 will be captured as a relatively high pressure normal to the sensing portion.

As shown in FIG. 2, the side-walls 22 engage directly with the portion of the human or animal body 7 to which the sensor is applied and thereby reduce sideways displacement along the surface of the body 7 and limit the depth of penetration of outer contact member into the surface of the body 72. In addition, the side-walls 22 retain the housing 2 in substantially fixed and stationary relationship to the body 7, such that during normal ambulatory activity and motion, the housing 2 and body 7 move substantially in unison.

Figure 3:
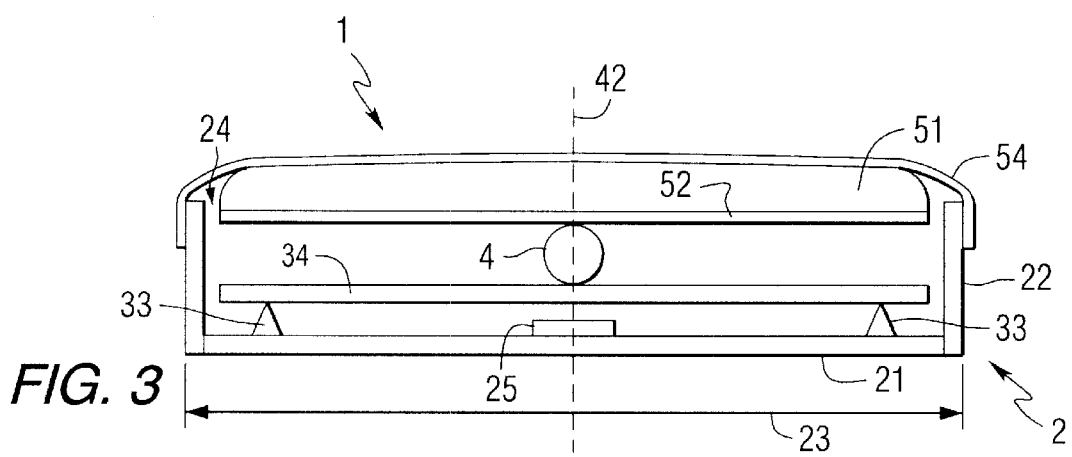
FIG. 3 is a schematic cross-section through a non-invasive sensing device in accordance with an embodiment of the present invention with outer contact member supported by a diaphragm and sensing a piezoelectric bimorph beam.

FIG. 3 illustrates an embodiment wherein a tough flexible diaphragm 54, made of a resilient material such as rubber, latex, plastic, elastomeric matrix composite or other elastomer, is mechanically attached or bonded to cover opening 24 defined by the side-walls 22. In this configuration, the diaphragm 54 serves both as a compliant return element to enable free orientation and topography accommodation by the outer contact member 51, and as an environmental shield to seal against incursion of dirt, moisture, corrosive and infectious agents and the like. In this example, the function of the sensing elements and the displacement member are combined in one structure, a piezoelectric bimorph comprising a metallic central vein with a thin piezoelectric ceramic layer on its upper and lower surfaces. The relatively low stiffness and high yield strain of the composite structure enables it to deflect significantly in the present mechanism and thereby generate readily measurable electrical signals in response to physiological excitation. Accordingly, the sensing portion comprises a piezoelectric bimorph beam 34, resting on pivot points 33 which are designed to support but in no way restrict the deflection of the piezoelectric bimorph beam 34. A displacement limiting stop, or snubber 25, is attached to the base 21 to limit the deflection and hence avoid permanent deformation or breakage of the beam 34.

Figure 4:
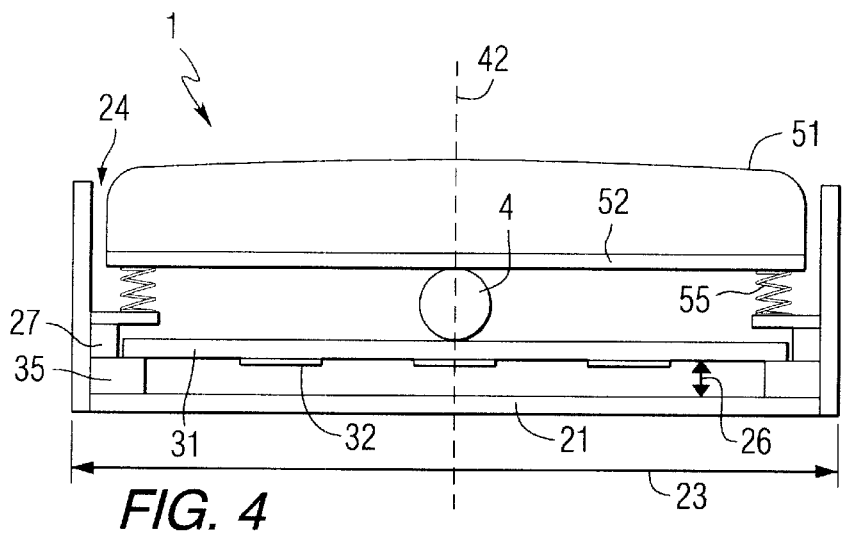
FIG. 4 shows a schematic cross-section through a non-invasive sensing device in accordance with an embodiment of the present invention with spring or foam mounted outer contact member and strain gages attached to an elastic beam.

FIG. 4 shows an alternative embodiment of the present invention wherein the interface transition mechanism comprises the outer contact member 51, attached to the stiffening member 52 as above, but compliant return means is provided by springy edge supports 55 which may be metallic or plastic springs, foam, rubber or other similar elastic or reversibly compressible material. In this embodiment, the load transfer element 4 comprises a short rod whose axis is in the plane of the stiffening member 52, attached to the stiffening member 52 and disposed perpendicular to the length dimension of the displacement member 31. The sensing portion comprises the displacement member 31 made of a material such as spring steel, bronze, stiff plastic or organic matrix composite with the attached sensing elements 32 made of conventional resistive strain gages or semiconductor strain gages, or piezoelectric crystal or piezoelectric polymer, such as PVDF or Kynar sheet, to detect deflection of the member 31. The separation distance 26 between the member 31 and the base 21 of the housing is made small enough to effectively mechanically protect the sensing portion by limiting deflection of the beam 31 and extension of the sensing elements 32.

Figure 5:
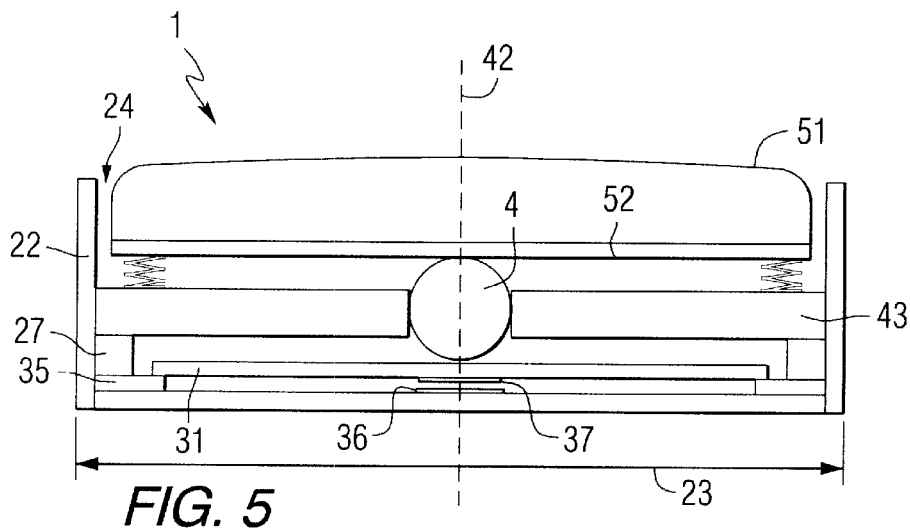
FIG. 5 shows a schematic cross-section through a non-invasive sensing device in accordance with an embodiment of the present invention with an integrally molded hard contact pad, ball bearing load transfer element, constrained sensing axis and capacitive displacement detector.

FIG. 5 provides an example of a device in accordance with the present invention wherein force components away from the sensing axis 42 are mechanically rejected. In many cases where signal sources other than the physiological source exist, these will present at a variety of impingement angles to the outer contact member 51, whereas the physiological signal under interrogation will appear primarily along the sensing axis 42. Accordingly, the magnitude of interference from noise, artifact, motion, etc, can be significantly reduced in comparison to the desired signal by constraining the device to transmit only those force components that lie along the sensing axis 42. Omnidirectional excitation received by the outer contact member 51 is mechanically filtered by constraining the load transfer element 4 to run in a well-lubricated tight tolerance machined channel or cylinder or guide comprising a lateral constraint 43. Displacement of the beam 31 causes a change in the relative proximity of conducting capacitor plates 36, which, in one embodiment, is conveniently measured as a capacitance change by connecting a moving plate 37 into a bridge circuit (not shown) with a high frequency oscillator (not shown) and observing the change in oscillator signal amplitude.

Figure 6:
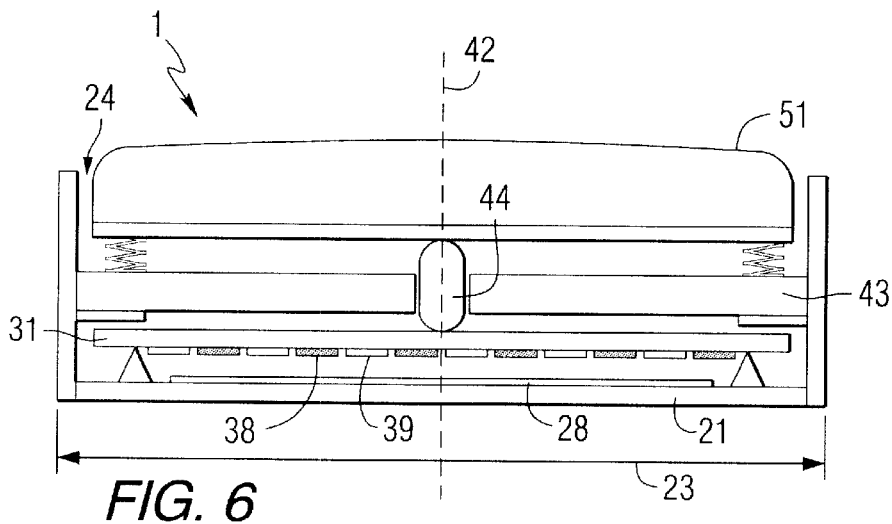
FIG. 6 is a schematic cross-section through a non-invasive sensing device in accordance with an embodiment of the present invention employing a hemispherically terminated piston as load transfer element, axially constrained in a medical cylinder and bearing on a flexible sensing beam with LED sources and photodetectors.

FIG. 6 depicts another piston and sleeve arrangement where a load transfer element 44 is constrained by the cylindrical hole in the support member 43 to respond in only the sensing axis 42. The load transfer element 44 is provided with rounded ends to minimize frictional transfer of off-axis activity to the sensing portion defined by the displacement member 31, photo detectors 38 and light emitting diodes 39. Displacement of the beam 31 relative to the base 21 is measured through the change in amount of light received by said photodetectors 38 as the emitter detector pairs 39 in the under surface of the beam 31 get closer to and further from the reflecting surface 28.

Figure 7:
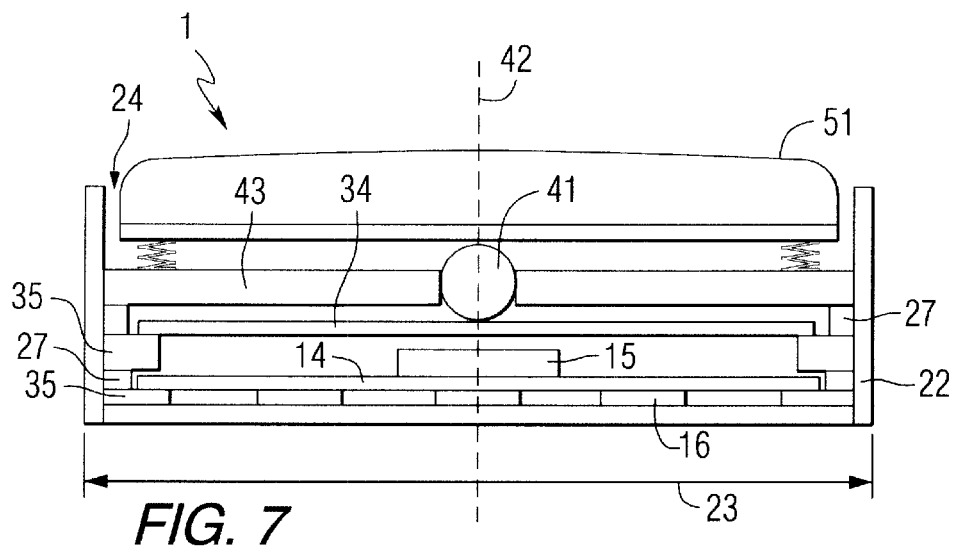
FIG. 7 shows a schematic cross-section through a non-invasive sensing device in accordance with an embodiment of the present invention using an axially constrained ball as load transfer element bearing on an end-mounted piezoelectric bimorph beam. Closely adjacent to the sensing portion and away from the body is another parallel bimorph beam configured as an accelerometer and resting on compliant pads.

FIG. 7 again illustrates an axially constrained system where a load transfer member 41 is a ball in a tight slot, bearing on an end-mounted piezoelectric bimorph beam 34. A parallel canceling member 14 of piezoelectric material, again potentially a bimorph, is provided as an accelerometer with a canceling mass 15 at its center to detect movement frequency, either for common mode cancellation or to supply frequency content that can be used, for example, by another subtraction scheme or digital notch filter to eliminate certain frequency ranges known to be rich in artifact signal. Compliant damping patches 16 may be interposed between the base 21 and the canceling member 14 to achieve some match between the mechanical impedance of the physiological load on the beam 34 and the elastomer bearing on the canceling member 14.

Figure 8:
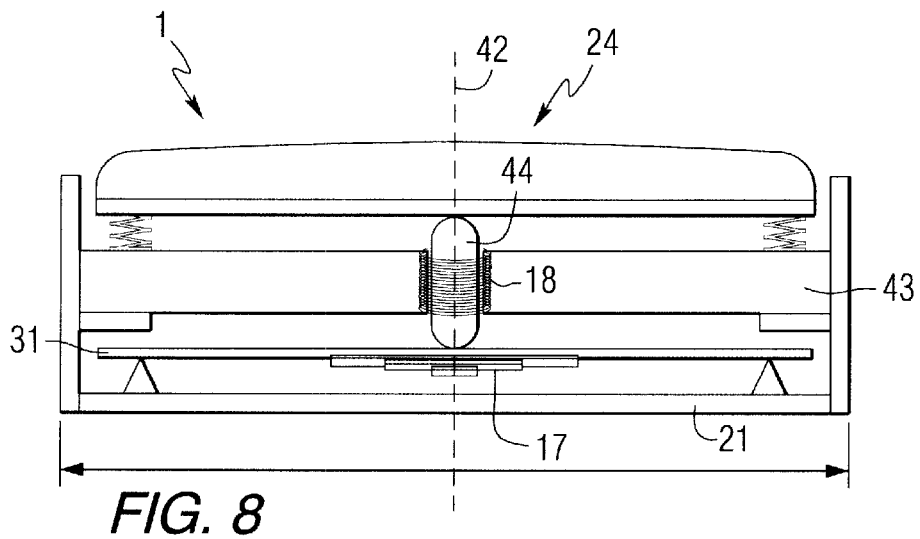
FIG. 8 shows a schematic cross-section through a non-invasive sensing device in accordance with an embodiment of the present invention wherein the load transfer element is an axially constrained ferromagnetic core material configured as an hemispherically terminated rod travelling within an electromagnetic coil and bearing against a pivot mounted leaf spring.

FIG. 8 shows how a similar geometry to that used in FIG. 6 may be employed with an axially constrained rounded rod 44 in the form of a ferromagnetic core running in a detector coil 18. In this instance, the rod 44 performs the function of both load transfer element and sensing portion, while lower leaf springs 17 and pivots 33 serve only as an inert return spring mechanism.

Figure 9:
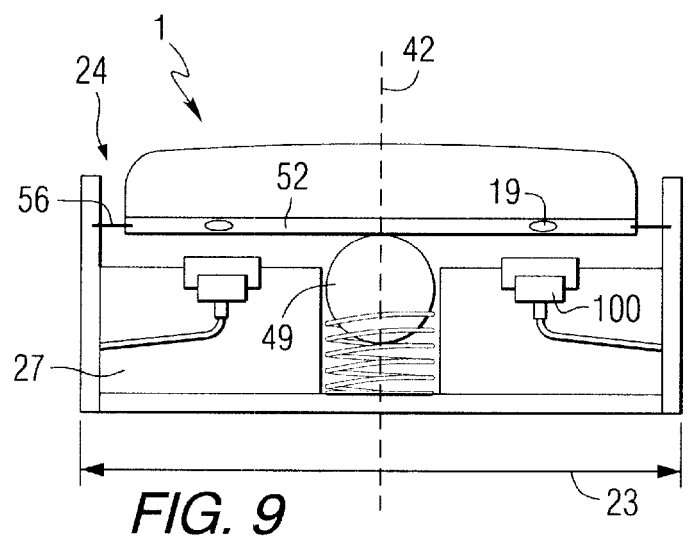
FIG. 9 is a schematic cross-section through a non-invasive sensing device in accordance with an embodiment of the present invention wherein the outer contact pad is suspended by edge flexures and rides on a spring loaded ball mount. The pad is outfitted with superficial magnetic elements facing towards eddy current detectors rigidly mounted with respect to the housing.

FIG. 9 illustrates a means of reducing the length dimension 23 of the device 1 by providing a compact return coil spring in contrast to a displacement member 31. A spring loaded ball 49 bears against the stiffening member 52 opposing inward travel of magnets 19 while edge flexures 56 serve both as compliant return elements and oppose outward travel of the magnets 19. The flexures 56 may be solid, such as metallic springs or elastomeric material, to also serve as an environmental seal. Displacement of the stiffening member 52 relative to housing spacers 27 is measured using eddy current detectors 100 which effectively sense the proximity of the small magnetic elements 19 in the lower surface of the stiffening member 52.

Figure 10:
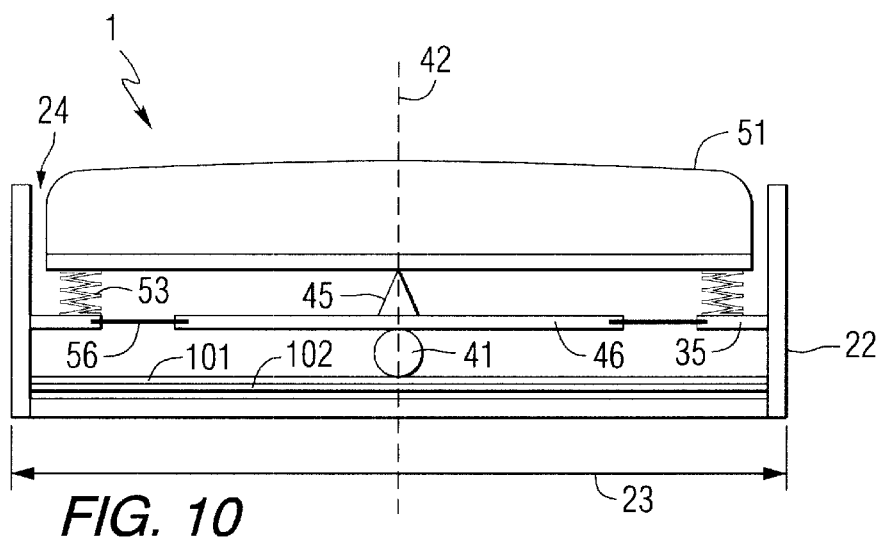
FIG. 10 shows a schematic cross-section through a non-invasive sensing device in accordance with an embodiment of the present invention showing how a PVDF sheet can be soft-mounted against the housing to pick up movement of a stiff flexure mounted beam through a small diameter ball contacter.

FIG. 10 provides an example of how the mechanical amplification scheme of the present invention can be used to generate significant signal strength when the sensing element is a sheet of piezoelectric polymer. Typically, polyvinylidene difluoride and other piezoelectric polymers, such as Kynar, have been applied in physiological sensing applications by direct contact of the material with the area of body over which the physiological signal is manifest. Although readings can be obtained, the material has too low a signal sensitivity and too high a noise floor to be useful in its own right as a sensor for purposes of the present invention. FIG. 10 show one example of how essentially pure axial force transfer can be ensured using the illustrated double sprung system, where compliant return elements 53 stabilize the orientation of the outer contact member 51 while flexures 56 and a rigid beam 46 reject off-axis motion components. A small diameter actuating ball 4 or edge produces high effective local pressure to deform a PVDF sheet 101 against its resilient but flexible backing 102.

Figure 11:
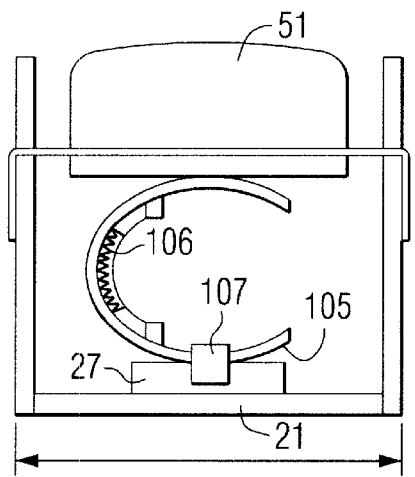
FIG. 11 shows a schematic cross-section through a non-invasive sensing device in accordance with an embodiment of the present invention wherein the electrical signal reflecting motion of a contact pad is generated by a strain gage attached to a springy element in direct contact with said pad.

FIG. 11 provides an example of a very compact, low part-count embodiment of the present invention where a single assembly 108 performs many of the functions of larger multi-component assemblies as described in other embodiments of the present invention. Thus, a multifunctional sensor assembly 105 serves as compliant return element, including a displacement member and a sensing portion 107. A piezoelectric element or strain gage 106 integrated into the structure serves as the sensing element. A diaphragm 54 provides coarse orientation and an environmental shield.

Figure 12:
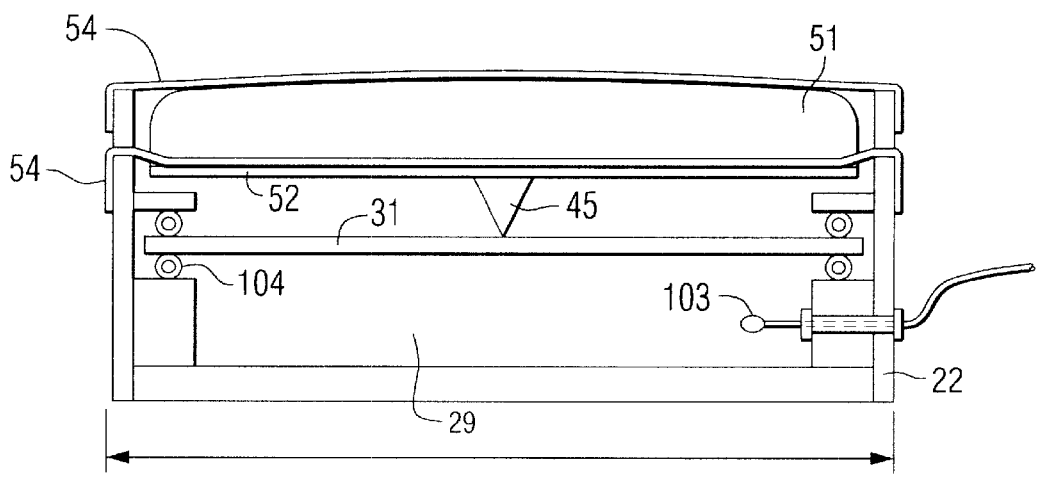
FIG. 12 is a schematic cross-section through a non-invasive sensing device in accordance with an embodiment of the present invention with multiple layers of environmental protection in the form of diaphragms and O' rings. Movement of a diaphragm-mounted contact pad is detected through a flexible plate over an hermetically sealed fluid reservoir incorporating a fiber optic volumetric pressure gage.

FIG. 12 shows one embodiment where particular attention has been paid to rugged environmental sealing both to keep external elements from the more delicate sensing portion and to prevent leakage of an encapsulated internal fluid chamber 29 which changes pressure upon sensed physiological forces. Two outer diaphragms 54A and 54B serve as fail-safe environmental shields as well as primary and back-up compliant return elements. Internally, a double O-ring seal 104 keeps a contained fluid 29 in place and again prevents incursion of external elements. Changing pressure in the fluid chamber 29 is sensed by any suitable isotropic pressure sensor 103 such as an optical fiber, the end of which is coated with a pressure sensitive chemical layer that alters the fiber end reflectivity and hence the amount of light getting back to a detector.

FIGS. 13A–D illustrate a preferred embodiment of the present invention viewed in side elevation in FIG. 13A, in plan view in FIG. 13B and implemented as a multiple device configuration in FIG. 13C. FIG. 13D shows a cluster of miniature sensing devices disposed across a band to maximize the possibility of acquiring a strong signal from one location. In FIG. 13A, the sensing device 1 is advantageously made very small by utilizing a miniature capacitive sensing element comprising conductive plates 36 and compressible dielectric material 109. Sensing element is compressed and changes in capacitance as displacement member deflects in response to physiological forces impinging on outer contact member 51. Displacement member 31 is designed to deform by less than the thickness of dielectric layer 109 in response to normal mounting pressure against the body. Because device 1 is small and circular in cross section it is possible to deploy two or more devices across the area of body where physiological pressures and displacements are manifest. As shown in FIG. 13C, this multiple configuration can be useful under circumstances where anatomical features limit accessibility of the pressures and displacements. In the example shown, the pulsating pressure waves emanating from artery 71 are effectively blocked and thus heavily attenuated by tendons 73 in the directions of devices 1A and 1C. However, the relatively soft springy elastomeric backing 119 enables device 1B to protrude into the soft tissue in the narrow channel between the tendons where the pressure wave is best presented. Optionally, in cases where interference is experienced from noise or motion artifact, signal purity and fidelity can be enhanced by subtracting the average signal from surrounding devices 1A, 1C, etc., which are picking up little physiological signal and instead receiving predominantly noise, motion artifact, etc. An additional important and synergistic benefit to the miniature sensor design depicted in FIG. 13A is that the ends of side-walls 22 facing the body and outer contact member all lie within a relatively small area of body surface and thus bear against material of very similar mechanical impedance. This is of great value in supporting the design consideration that artifact signals like bodily motion will have equivalent impact on housing 2 and interface transition mechanism 5, hence making device 1 effectively self-canceling for these phenomena, whereas physiological displacements are captured primarily on outer contact member 51 and are thus clearly differentiated from housing response. In contrast, if a larger sensing device is used in FIG. 13C, there is a possibility that outer contact member could be largely in communication with the soft tissue channel over artery 71 while side-walls rest over tendons 73. This places the sensing portion and its mechanical reference (housing) in different mechanical impedance environments and impairs the above referenced self-canceling effect.

FIG. 14 shows a short axis (14A) and long axis (14B) section through a sensing device in accordance with the present invention designed with features similar to FIG. 3 but incorporating lateral constraints 34 for off-axis rejection. The device is equipped with both a physiological sensing portion 34A sensitive to displacement of outer contact member 51A and a canceling sensing portion 34B sensitive to displacement of outer contact member 51B and hence responsive only to gross motion of the whole device. Motion, noise and other artifacts are sensed at approximately the same level at 34A and 34B whereas physiological displacement can only effect 51A. Consequently, subtraction of the voltage developed at 34B from that developed at 34A effectively reduces the signal component due to non-physiologic effects.

FIG. 15 is a cross-sectional view of a device in accordance with the present invention designed primarily for sensing acoustic phenomena such as heart, lung and bowel sounds. In contrast to a conventional stethoscope which is sensitive only to relatively low frequencies in the audio band, this device maintains level sensitivity from below audible frequencies through to 10 kHz and above. It should be noted that flexible diaphragm 54 serves the function of outer contact member 51 in this design where sounds rather than displacements are being examined. Outer contact member 51 is not necessary because the above referenced acoustic phenomena appear fairly evenly across an area of body surface as distinct from displacement phenomena such as arterial pulsations that derive from a small source, are directional and only present strongly at specific locations. Since the requirement for omnidirectional response and signal capture at any point on the area of outer contact member has thus been removed, load transfer member 4 no longer has to accommodate the type of free rotational movement needed to detect displacement phenomena. Accordingly, the principal design constraint is maximum acoustic transfer through to sensing element and for this purpose, load transfer member can be optionally bonded to stiffening member and sensing element 34. It should be noted that while outer contact member is not employed, the flexible diaphragm allows a certain amount of conformation to anatomical contour. The configuration illustrated is useful as a sensing device for a pediatric stethoscope, particularly for neonates and very small pre-term infants, where the dimensions of the device can be made extremely small enabling local placement with good contact on small very curved body parts. A device constructed in accordance with this embodiment has been tested on newborn children and found to have sensitivity beyond that of a conventional neonatal stethoscope in picking up previously inaudible sounds from the bowel region associated with digestive and elimination processes and previously inaudible clicking type sounds from the heart.

FIG. 16 shows a sensor similarly constructed to that described in FIG. 15 but equipped with passive means for rejecting external noise and artifact variety of sources. Mechanically transmitted vibration from cable sheath motion against clothing, for example, is de-coupled from the sensing device by providing outer casing 110. Cable insulating sheath 118 is tied firmly to outer housing while the contained signal wires are embedded in a soft elastomer 119 hereby preventing any mechanical vibration from getting into sensing device. Rubbing noises from frictional forces against the outside of housing 2 are similarly excluded by the poor transmitting characteristics of the barrier provided by casing 110 and elastomer 119. Outer casing 110 also serves as an acoustic shield to prevent extraneous room noise from vibrating element 34. The sensing device so described is useful in characterizing respiratory phenomena, for example in the upper airway and lungs and can be employed to assist in sleep disorder diagnosis, placement of endotracheal tubes, monitor individuals as they are weaned from artificial respirators, etc. The very high sensitivity also makes these devices useful in detecting and diagnosing very subtle cardiac phenomena.

Figure 17:
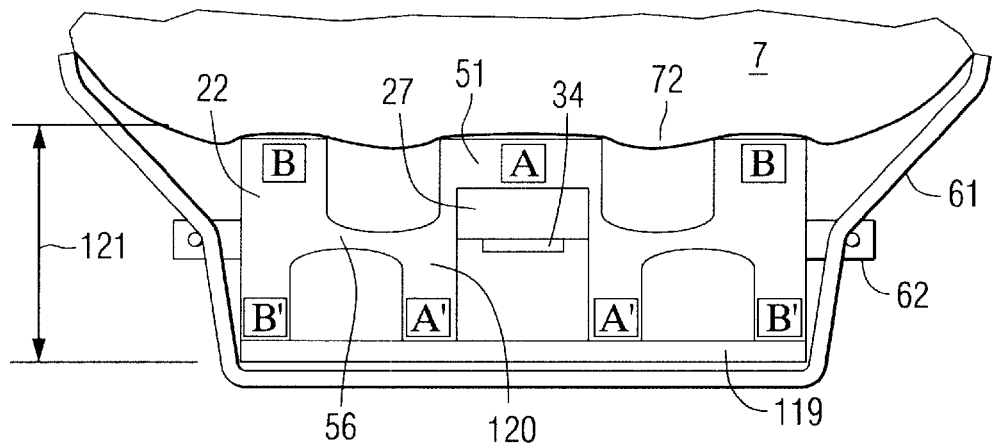
FIG. 17 is a conceptual drawing of a cross-sectional view of a sensor in accordance with the present invention specifically designed to be resistant to motion artifact.

FIG. 17 is a conceptual drawing of a cross sectional view of a sensor in accordance with the present invention specifically designed to be resistant to motion artifact. Movement and other sources of interference are rejected through self-cancelation by providing a mechanically equivalent environment for the sensor assembly (interface transition mechanism, load transfer member and sensing portion) and the housing relative to which it moves. Note, load transfer element is hidden by support 27 in this drawing. All motion is thus received equivalently at the sensing element and the housing and will be rejected as a common mode. To accomplish this, both sensor assembly and housing 2 have equal mass, and equal area bearing against the skin of the body, i.e. area A is approximately equal to the sum of the two areas labeled B. The center of mass of the whole assembly is engineered to be collocated with the sensing element (34) at the central position in the height of the device (121) in the same plane where the tabs (61) for the retaining strap are located, thereby eliminating the effect of any difference in momentum between the upper and lower halves in response to movement. The area of housing at the back of the device (the sum of the two areas labeled B') and the area of the ends of the side rails 120 bearing on the back of the device (the sum of the two areas A') are also made equivalent. Both areas rest equally on backing member 119 which is preferably a soft elastomeric material to enable free movement of rails 120. Accordingly, both housing and sensor assembly react against an equivalent mechanical impedance. It should be noted that flexures 56, shown as thinner portions of the monolithic structure must be very compliant to enable easy relative movement between housing portions labeled B and B' and sensing assembly A and A'.

Figure 18:
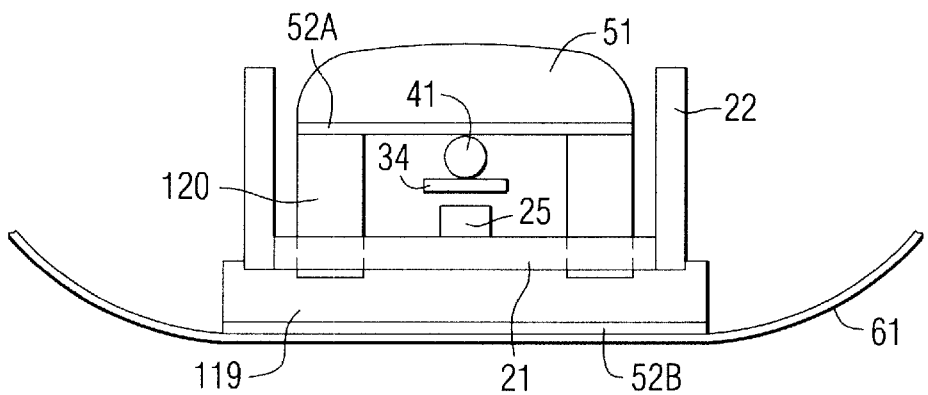
FIG. 18 shows a practical implementation of the concepts provided in FIG. 17. Side rails attached to outer contact member react against the same backing as the housing.

FIG. 18 shows a practical implementation of the concepts provided in FIG. 17. Housing (21, 22 and 25) and sensing assembly (51, 52A, 41 and 120) bear with equal area and equal mass against compliant backing 119 which is supported by stiffener 52B and application strap 61. Side rails 120 are attached to stiffener 52A and slide through clearance slots in base 21 to achieve the equivalent reaction between housing and sensing assembly.

Figure 19:
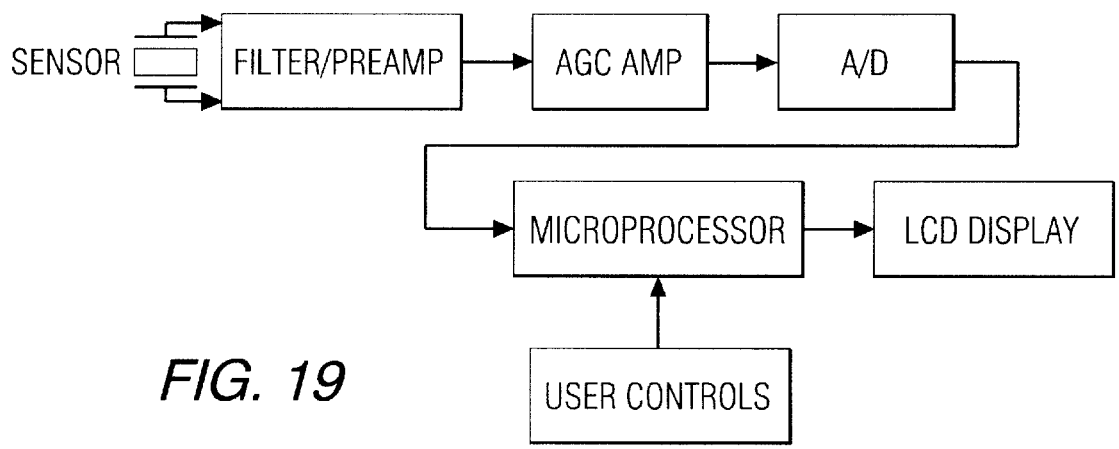
FIG. 19 shows the logical flow of measured signals through the analog and digital electronic circuits.

FIG. 19 shows the logical flow of measured signals through the analog and digital electronic circuits.

Figure 20:
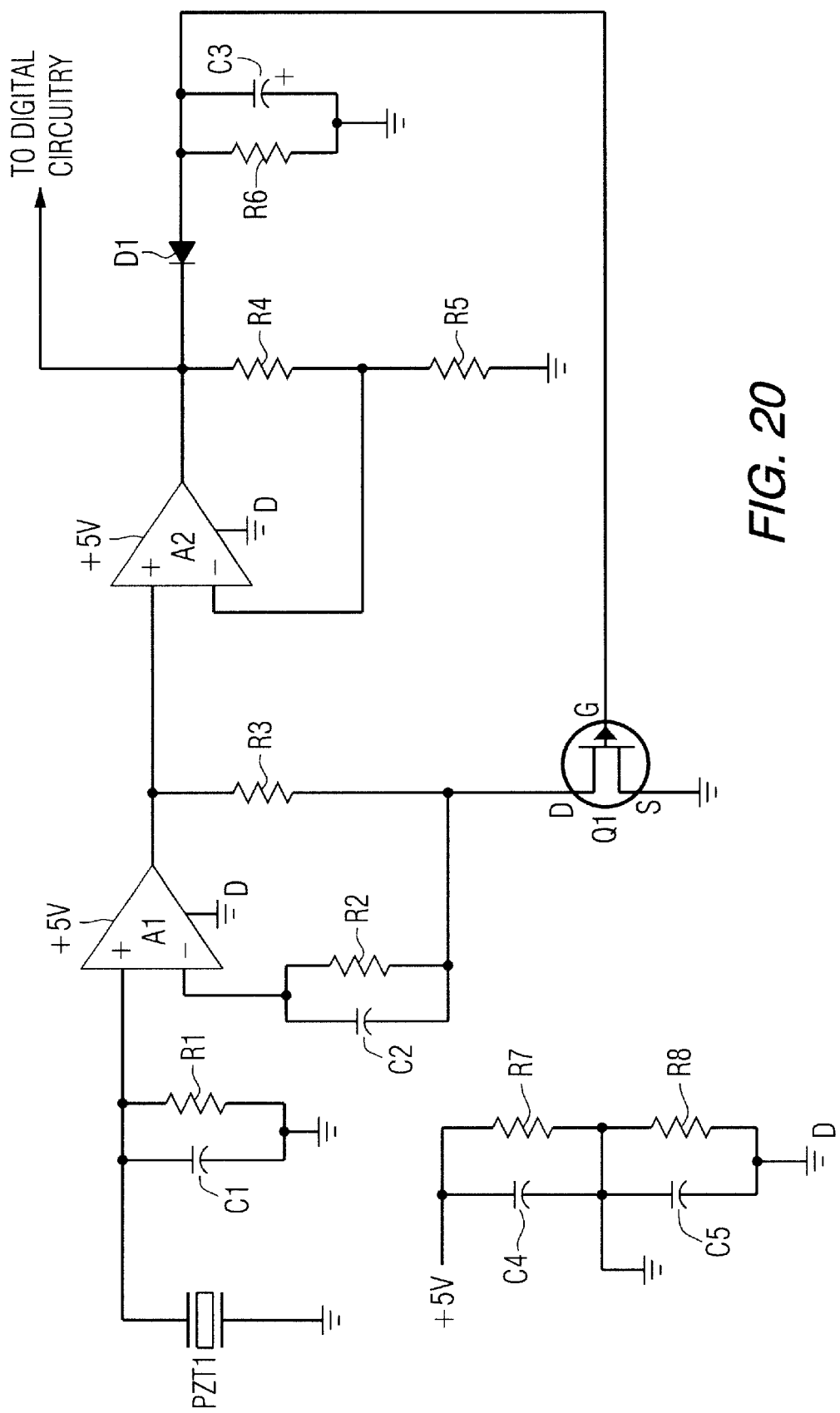
FIG. 20 is a schematic of the analog electronic circuit used to condition signals prior to digitization and processing.

FIG. 20 is a schematic of the analog electronic circuit used to condition signals prior to digitization and processing. In many applications of the sensing device of the present invention, the signal received directly from the sensing element is all that is needed and can be measured or displayed with any conventional electronic instrumentation. In embodiments of the present invention where the signals deriving from physiological events must be subjected to computational processing, to determine peak to peak intervals, for example, the present circuit is usefully employed to adapt the signals optimally for receipt by the digital electronics. The apparently disconnected circuit at the bottom left of the figure is a voltage divider which enables a single 5V supply to be used. To avoid complicating the schematic this is shown separately, but is actually connected to each point in the main circuit where corresponding symbols are shown, such as "5V" and ground.

Figure 21:
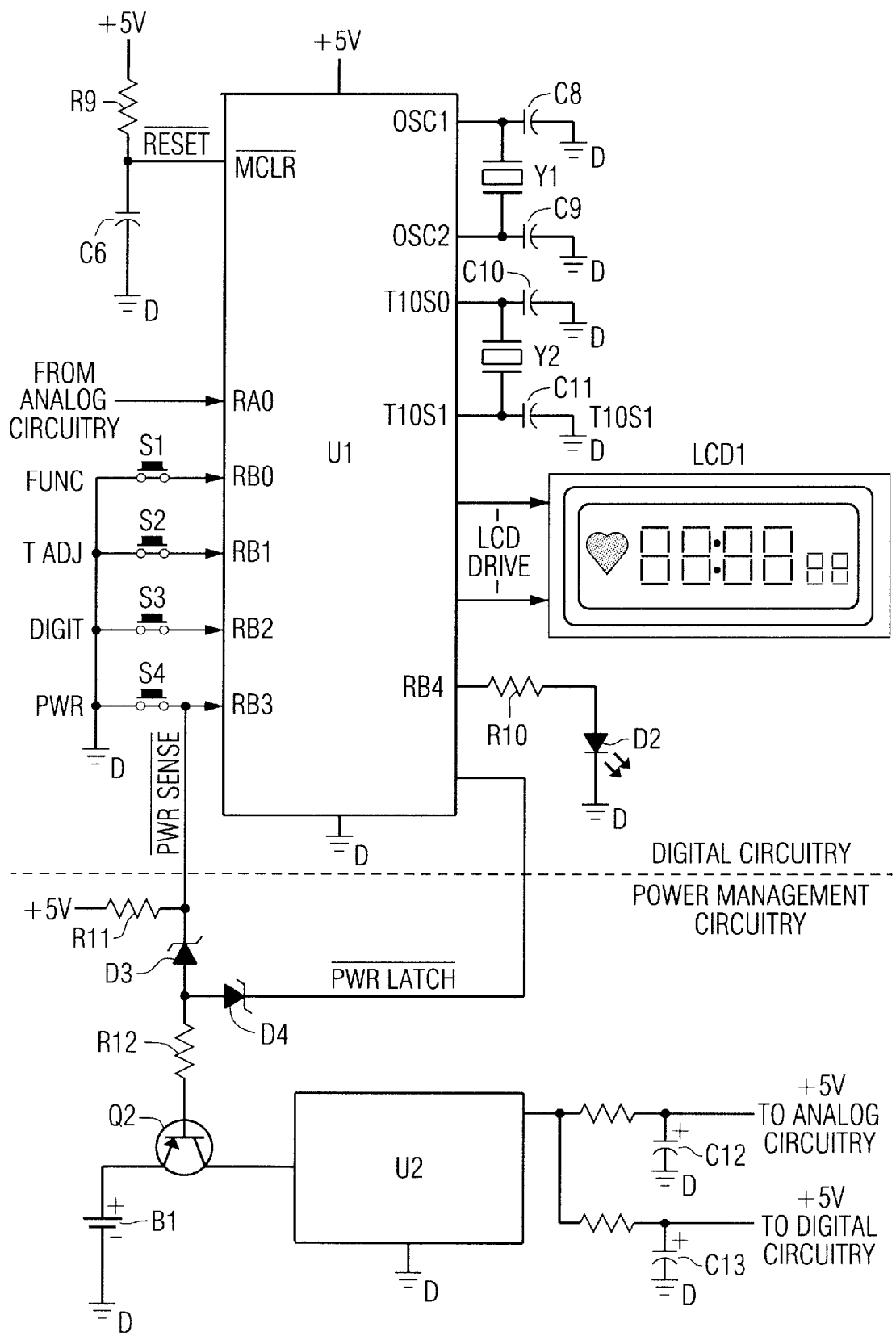
FIG. 21 is a schematic of the digital electronics used to apply computational processes to the digitized signal such as peak recognition, interval timing, application of logic rules, signal processing and rate calculation.

FIG. 21 is a schematic of the digital electronics used to apply computational processes to the digitized signal such as peak recognition, interval timing, application of logic rules, signal processing and rate calculation.

Figure 22:
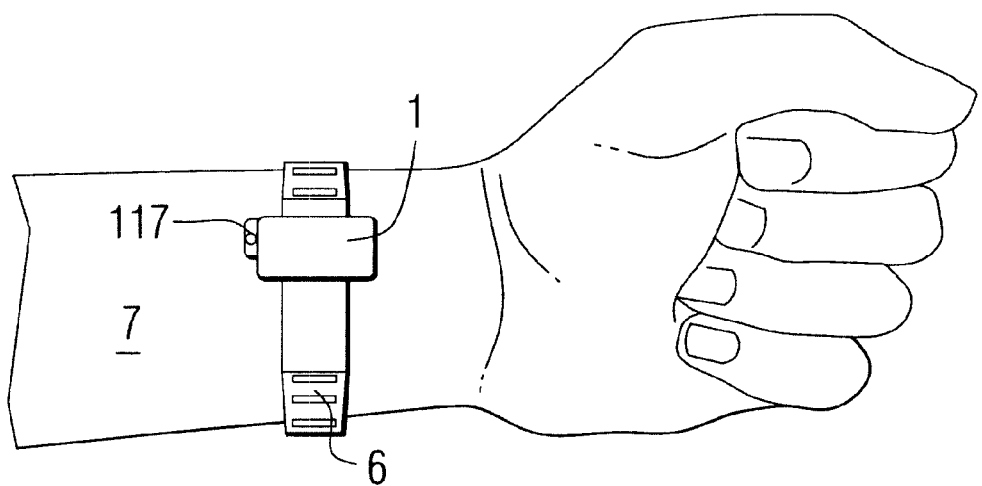
FIGS. 22 and 23 schematically illustrate a wrist mounted heart rate monitor in accordance with an embodiment of the invention.
Figure 23:
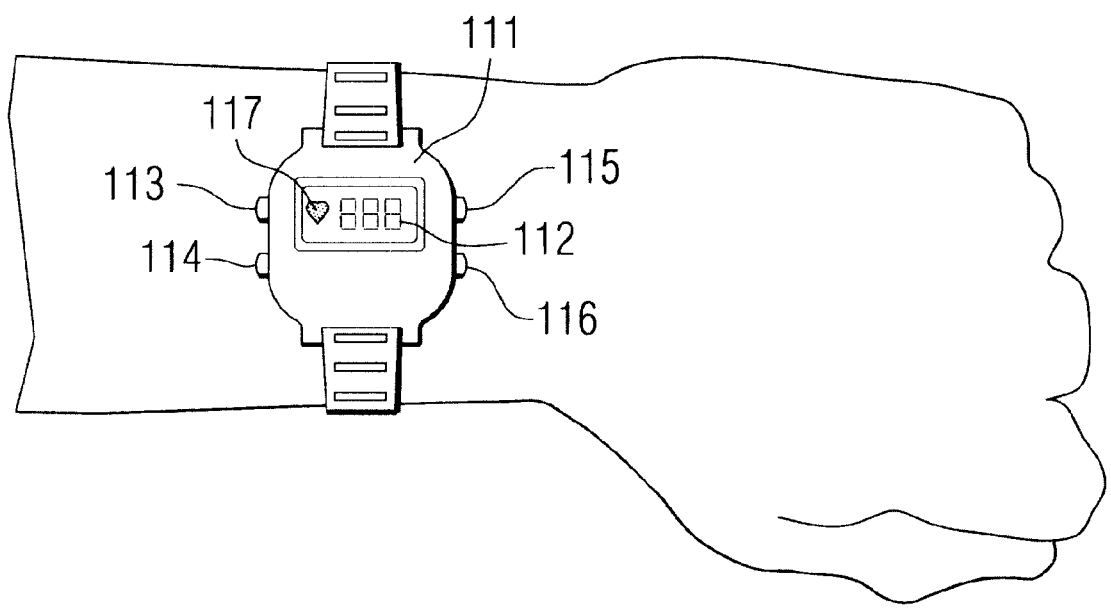

FIGS. 22–23 depicts an embodiment of the present invention wherein the sensing device is applied over the radial artery on the wrist and used to calculate heart rate based on timing the interval between the displacement pulses generated as a bolus of blood propagates down the arm. User controls 113, 114, 115 and 116 are provided on watch case 111 for adjusting time, heart rate limits, switching off power to the heart rate function and changing mode. Placement indicator 117 flashes a display on the upper and lower surface of the wrist whenever a signal peak is determined by the digital electronics and confirmed by the processor. The user can observe the indicator for steady flashing at approximately the expected heart rate and use this as a guide to correct initial positioning.

The above examples and associated drawings are merely provided as illustrative examples and are not intended to limit the scope of the present invention. It would be clear to one of ordinary skill in the art that each of the described embodiments contains features and mechanisms that could be used interchangeably in other embodiments to provide equally effective results.

While the above description covers exemplary embodiments of the sensing device of the present invention, illustrating the flexibility in design and arrangement of the various different components, certain general principles apply to each component as described below.

Housing

The housing 2 provides a tough protective barrier between the customary forces and impacts imparted by the normal external ambulatory environment and the delicate, fine and intricately configured internal components. It also provides a rigid structure against which to mount the various sensing components, each of which must be maintained in a substantially constant and precisely fixed spatial relationship with the others. The housing 2 is also used to interface the device to a strap or other means, such as adhesive tape, to hold the device in intimate contact with the body, and to locate and fix the device on the area of the body surface where the physiological effect can be detected by limiting lateral displacement of the device. The height of the sidewalls 22 in relation to the protrusion of the outer contact member 51 also prevents damage to the device by limiting the inward displacement of the interface transition mechanism when the device is forced against the surface of the body. When pressed against the body, the housing 2 also serves to provide a substantially constant spatial relationship between the internal mechanical and sensing components bearing against the body and their reference or attachment point in the housing which is also bearing against the body. By providing a substantially stationary relationship between the device and a human or animal body, much of the external noise and motion is received equally on the sensing element and the housing against which it references, and the potentially interfering effect is therefore canceled automatically as a common mode.

Interface Transition Mechanism

The interface transition mechanism 5 provides a highly compliant means of mechanically coupling between the human or animal body and the load transfer element 4 which bears on the internal sensing portion. As with the other components of the device, it is designed to be extremely light and compact to accommodate the requirement that the device be unobtrusive, portable and preferably wearable for long periods without adverse effects. The overall function of the interface transition mechanism is to collect any and all subtle forces and displacements over a relatively broad area on the body and focus them down onto the load transfer element. The specific compliance of the interface transition mechanism is important both for efficiency of load transfer across the anatomical-to-inanimate interface between the device and the body and for long-term comfort on the wearer. Compliance of the device is optimized for the physiological sign under investigation and the anatomical feature where the device is placed. The optimization process for any given body location and physiological sign would be routine for one of ordinary skill in the art and typically comprises an iterative experimental process in which the best compromise is achieved between highest possible signal level, minimum response to noise, and user comfort. Parameters that may be adjusted in order to tailor the compliance include the elastic modulus of all components in the mechanical loop between the housing interface to the body and the outer contact member interface to the body. These compliances include the stiffness of the housing and pivot points, the stiffness of the displacement member and sensing element, the stiffness of the load transfer element, and the stiffness of all components of the interface transition mechanism, ie., the outer contact member, the stiffening member and compliant return elements.

The interface transition mechanism 5 may comprise an outer contact member 51, compliant return elements 53 and optionally a stiffening member 52. The outer contact member is formed to the approximate shape necessary to mate uniformly with the anatomical feature at the point on the body where physiological signals are received. The member may be made of any light rigid material, such as hard plastic, wood, composite or thin metal, contoured to the natural curvature of the body and subcutaneous structures. Alternatively, the member 51 may comprise a softer, more flexible, material such as rubber, silicone, epoxy, urethane or other resinous plastic or composite, formed to the appropriate shape and supported against a high modulus stiffening member. The inherent stiffness of said former rigid member or, in the case of softer outer contact members, the stiffness imparted by the stiffening member, ensures that any displacement or force incident on any portion of the surface of outer contact member is faithfully transmitted to the load transfer element. The outer contact member 51 and stiffening member 52 may be bonded or attached to each other or may be a simple mechanical placement fit as shown in FIG. 3 where the downward clamping force from the diaphragm is enough to hold the stiffening member in place.

The compliant return elements 53 serve as essentially the only structural support for the outer contact member 51 (and optional stiffening member 52) and may comprise mounting springs, flexures or pads of resilient elastic material, or may be a suspension arrangement employing, for example, a resilient flexible diaphragm to which outer contact member and stiffening member are attached. In either case, whether composed of springs or diaphragm, the compliant return elements 53 provide an essentially isotropic mounting scheme, and while somewhat constrained laterally in the plane of the opening 24 in the housing 2, the return elements 53 enable outer contact member to move freely in almost any direction in response to a physiological displacement incident on said contact member from any orientation. Accordingly, interface transition mechanism responds omnidirectionally over all of its surface. The isotropic mounting scheme has the added advantage that it will orient and conform to anatomical contour to produce intimate contact and comfortable location against the body.

The outer contact member 51 is placed in intimate contact with, and in a stationary relationship to, a portion of the body surface 72 wherein the portion is in close proximity to the organ or tissue that is the source 71 of the physiological process. The outer contact member 51 is provided with a broad enough area of interface to encompass a large and representative area on the body surface over which the effects of the physiological process are manifest and detectable.

Load Transfer Element

The mechanical load transfer element 4 is provided to apply the displacement received at any point on the surface of outer contact member 51 through to the internal sensing portion 3. The mechanical load transfer element also magnifies the effective force on the displacement member 4 by applying the mechanical load received from the outer contact member 51 onto an area of the displacement member 31 smaller than the outer contact member area. The mechanical load transfer element 4 efficiently applies the force either onto an easily deflected portion of the displacement member 31 where it is detected by the sensing element 32, or directly onto a sensitive portion of the sensing element. The mechanical load transfer element 4 is typically a rod or ball or sharp edge or cone tip, and transfers any force (incident from any direction on outer contact member) onto the sensitive region of the displacement member 31 or sensing element 32.

The mechanical load transfer element 4 may be held loosely in position with simple mechanical constraints or may be attached at one end to either the outer contact member 51 or the displacement member 31. However, to satisfy the condition that the interface transition mechanism be essentially free-floating without directional constraint, the other end of the mechanical load transfer element 4 must either be free, or retained only in a ball and socket or a universal joint or the like.

In other embodiments, for example, as illustrated in FIGS. 5, 6, 7, 8, 9, 10, the rod or ball or other load transfer element is constrained to move only in one direction, along the axis 42 between the physiological signal source and the sensitive potion of the sensing element. Thus, while the outer contact member 51 is receiving and responding to forces over a broad area and from all directions, it transfers to the sensing portion 3 only those components substantially parallel to the sensing axis 42, thereby rejecting off-axis excitation such as gross bodily motion, artifact and noise. The constraint 43 used to prevent lateral movement from this axis 42 may be in the form of mounting flexures, a rod and ball-race, a close tolerance well lubricated piston and cylinder arrangement, a magnetic suspension bearing or the like. With a lateral constraint of this type in place, the upper and lower ends of load transfer element must be rounded and smooth to engage smoothly with outer contact member and inner displacement member. Alternatively, the ends may be mechanically engaged with said members using any type of omnidirectional joint such as a ball and socket, spherical joint, or simple universal joint.

Sensing Portion

Sensing portion 3 serves to produce an electrical signal when there is displacement, motion, bending, deflection, compression of sensing element by the load transfer element, or when deflection of the displacement member is detected by any of a variety of electrical, magnetic or optical means.

The design and properties of the sensing portion 3 are critical determinants in the size and function of the physiological sensing device of the present invention. The overall design of the device is controlled by optimization of the balance between two competing factors. On the one side, mechanical impedance matching for high signal and high signal-to-noise ratio favors a low modulus sensing portion yielding high displacements of the sensing portion. However, overall device height constraints from base to outer contact member necessitate very small displacements of the sensing portion, hence high stiffness and large signals in response to small motion of said sensing portion. Another critical design factor that must be considered in performing the above optimization is that sensing portion must have extremely wide dynamic range to accommodate the relatively large DC bias force that will always be present because the device bears against the body and still be able to respond to the small forces and very subtle fluctuations associated with physiological phenomena.

Because the physiological forces and displacements are typically extremely small, it is important to employ the most sensitive of sensing means and to actuate the sensing element 32 at a very sensitive portion. Accordingly, to maximize signal level and thereby improve signal to noise ratio, the mounts or pivot points 33 for the displacement member 31 and/or sensing element are substantially fixed in location with respect to the housing 2. This arrangement ensures the greatest possible signal from any force or displacement incident on outer contact member 51 and transmitted through load transfer element 4.

Exemplary sensing portions are described in the following section. Using a displacement member in the form of an end-mounted beam or plate or a circumferentially mounted disk as illustrated in FIGS. 3–12, a variety of techniques can be employed to measure the beam deflection from its unstressed or resting bias position. It should be noted, for a given sensing technique, that the sensitivity and compliance of this system can readily be adjusted through use of different modulus and thickness construction materials and by moving the pivot points. Another important design consideration is the mounting technique used at the pivot points or at the ends of the beam, plate or similar structure. Because the forces and deflections are so very subtle in response to physiological processes, displacement of the member cannot be impeded in any way, and the mounting structure at either end of the beam must be fully unconstrained. Accordingly, for stiffer beam materials, simple mechanical pivots and loose end slots are appropriate, while rigidly clamped, bolted or bonded ends will significantly diminish the amplitude of received signal. The orientation of the displacement member in the plane perpendicular to the sensing axis does not effect the performance of the device and can be arranged to best accommodate the size and geometric constraints of the particular application.

Beam deflection may be detected as illustrated in FIGS. 1, 2, and 4 by bonding resistive or semi-conducting strain gages or piezoelectric wafers to the surface of the beam. In another embodiment, illustrated in FIG. 5 a conductor disposed on the underside of the beam and another attached to the base 2 of the housing, are placed in an electrical circuit as two opposing plates of a capacitor. A standard bridge circuit with a high frequency oscillator may be used to measure the change in capacitance as the beam deflects. FIG. 6 shows an optical arrangement for sensing the proximity of the deflected beam to the housing wherein an array of transmitters, such as light emitting diode transmitters and adjacent photo-detectors (for example phototransistors) are used to determine the change in electromagnetic absorption as the sources and detectors move towards and away from a reflector on the inner surface of the housing. Another technique is shown in FIG. 8 where the load transfer element 44 also serves as a magnetic core running through an electrical coil for gaging beam deflection. In FIG. 9 the deflection of a displacement member is measured using eddy current detectors to determine the proximity of small magnets in stiffening member from a referencing structure attached to the housing.

Alternative sensing means to gage transmitted displacement include the use a fiber optic pressure sensor in a fluid chamber encapsulated between the housing and a hermetically sealed displacement member as shown in FIG. 12. Another technique shown in FIG. 11 is to use a suitable geometry of spring element, in this case a split cylinder with attached strain gage, to combine the functions of load transfer element, displacement member and compliant return elements. Yet another is to measure the electrical output from a soft mounted piezoelectric polymer sheet, such as Kynar or polyvinylidene difluoride (PVDF) as it is deflected at its center by load transfer element as shown in FIG. 10.

A preferred embodiment of the invention shown in FIG. 3 employs a displacement member in the form of a beam 34 that also serves as the sensing element because it is constructed of an electroactive material such as a piezoelectric crystal, piezoelectric bimorph, piezoelectric unimorph or PVDF on a stiff backing. As the beam 34 moves, an electrical signal is generated in proportion to the amount of displacement transmitted by load transfer element.

EXAMPLE 1

Measurement of Heart Rate at the Wrist

One advantageous use of the sensing device of the present invention is in a wrist-worn pulse rate measuring device such as shown in FIGS. 22 and 23, that is continuous reading, autonomously operating without user intervention, and wholly self-contained in a small and unobtrusive package on the wrist, including detector, electronics, power supply and display. This embodiment of the invention addresses and overcomes the shortcomings both in commercially available pulse measurement devices and in previous attempts to develop autonomous pulse counting devices for the wrist. Specifically, the device: is relatively tolerant of imprecise location and reads adequate signal even when displaced slightly from its ideal position centered perfectly over the radial artery on the volar aspect of the wrist; works satisfactorily over a wide range of absolute input signal level and signal to noise ratio because it automatically adjusts its sensitivity to accommodate the wide range of signal magnitudes encountered in practice due differences between individuals, health and physiological differences, poor positioning and wrist orientation; requires little or no complex signal processing and computation to learn and recognize pulses because the sensing device provides clean signals with high fidelity replication of arterial wall motion; and is relatively insensitive to motion artifact by virtue of a mechanical design which effectively rejects gross motion that couples equally into the sensor element itself and its support housing.

The above described attributes of the device are enabled by two critical elements: 1) a novel sensor design that is compact, comfortable, and responsive to incident excitation from all directions over a wide area; and 2) detection electronics that rapidly self-adjust to the pulse signal strength as it varies over orders of magnitude from individual to individual and within an individual during position changes, activity, etc.

Sensor

In order to maximize sensitivity to the local physiological displacements and pressure in the vicinity of the radial artery during an arterial pulse event, and minimum sensitivity to other extraneous effects, a sensor was developed with the following features.

Local Conformity and Omnidirectional Response

As described above and shown in FIGS. 1–12, an interface transition mechanism was developed that enabled excitation from any direction, incident on outer contact member to be transmitted onto the sensing element. Essentially free mounting the outer contact member and associated stiffening member using compliant return elements enables the interface of the sensing device 1 to conform to the local topography at the surface of the body without compromising effective load transfer.

Adjustment of Mechanical Compliance to Maximize Sensitivity to Physiological Phenomena The sensing portion 3 and its actuating mechanism, comprising interface transition mechanism 5 and load transfer element 4, were selected and designed such that the typical flesh displacement and force accompanying an arterial pulse wavein a normal wrist produced a corresponding displacement at the sensor element. For example, the mechanical impedance of the assembly in FIG. 3 (a mechanical impedance circuit comprising the mounted piezoelectric bimorph sensing element, the load transfer element and the interface transition mechanism bearing against the skin of the wrist) was tailored to closely match the impedance of the artery, flesh and skin of the wrist by adjusting each of the elements of the mechanical impedance circuit until the normal range of physiological displacements (from quiescent individual with a weak pulse to active individual with strongly presented pulse) was reflected in the widest possible range of signals from the sensor element while at the same time ensuring that the force used to apply the sensor to the body did not exceed the measurement range of the sensing element. The coupling achieved in this manner between the sensor and the physiology is so good that the device can be used without coupling aids such as liquids or gels or foam interfaces between the device and the body. The bimorph element was selected to be extremely thin and compliant and was configured as a narrow bar suspended at its ends to enable maximum deflection at low force via contact at its center.

Force Maximization

Because the amount of pressure and displacement produced by the radial artery are relatively small, the load transfer element design (a thin rod transverse to the length of and resting against the bimorph beam) enabled forces collected over a large contact area on the surface of the body over the artery to be received at a significant force level at the sensor element. Effectively, the mechanism collected a force over a large area and concentrated it down into a small thin line contact at the point of maximum moment —the center of the bimorph element.

Satisfactory Operation Even with Imprecise Location

In many individuals, the position at which the arterial pulse is presented (usually detected by feel, or palpating) is difficult to locate. In addition, the optimum location changes as the wrist is rotated, repositioned and moved. Accordingly, the best physiological signal is not necessarily fixed at a given location. Thus, the sensor was designed not only with a broad pick-up area but with a mechanism that ensured that a deflection due to pulse at any point over that area and from almost any angle of incidence was effectively translated down onto the center of the sensing element. This was accomplished with the aforementioned quasi free-floating outer contact member which not only conforms to anatomical contour but transmits all forces into load transfer member.

Decoupling of Gross Motion

Because the very subtle low force displacement caused by the arterial pulse has to be detected in the presence of the user's gross motion and vibration, the sensor was specifically designed to have least sensitivity to these movements to these movements. For this purpose, the mass of all components of the device was minimized thereby decreasing any force on the working components of the device. A very light bimorph element and light sensor housing were chosen to minimize accelerometer —type pick-up from motion of the element or motion of the housing. In addition, the geometrical design of the sensor ensures that both the housing and the outer contact member (hence the piezoelectric element) are firmly mechanically coupled to the flesh of the wrist. Consequently, as the user moves and the flesh of the wrist moves correspondingly, this movement is translated equally into the sensing element and the housing. Accordingly, the signal due to relative movement between the element and its mounts (on the housing) is minimized. This effect is optimized by ensuring mechanical equivalence on either side of the sensing element —the action side defined by interface transition mechanism and load transfer member —and the reaction side defined by the sensing element support mechanism and housing. Thus it is beneficial to ensure that the area of outer contact member disposed against the body is essentially equivalent to the area of the ends of housing side walls disposed against the body. Similarly, the mass of the housing and sensing element support mechanism should be essentially equivalent to the mass of interface transition mechanism and load transfer member.

Maximum Energy Transfer Into the Active Element

It should be noted in the design of the mechanical impedance matching circuit (described above with reference to FIG. 3) that all of the components between the skin and the sensing material combine as a relatively compliant mechanism with impedance compatible with the physiology under test. In contrast, the sensing element and its support mechanism are essentially infinitely rigid and hard thus ensuring that none of the coupled energy is lost in the mounts or actuating members. In other words, the impedance matching is accomplished in the mechanical elements that come in advance of the sensing elements which is then configured to capture all of the sensed displacement.

Electronics

Experimental observation has shown that there is a tremendous range in the strength of the pressure/displacement signal measured over the radial artery on the volar side of the wrist as a bolus of blood passes under the sensor. This is the case even using the high sensitivity and high signal to noise pick-up device described above. This range derives not only from differences between individuals, but also from changes due to physical activity hence heart rate and blood pressure, and loss of signal strength as the wrist is rotated into different positions. Accordingly, the pulse detection and counting electronics need to handle inputs all the way from easy to detect large sensor voltages that are well in excess of the noise floor to very small voltages where the signal to noise ratio is extremely low and it is hard to discriminate the pulse from other extraneous signals. Previously disclosed wrist pulse monitors have failed to recognize the magnitude of this challenge and therefore to provide the type of circuits that automatically track rising and falling peak signal amplitudes and respond instantaneously by adjusting the amplifier gain to normalize the output. This is especially important for passing the signal to the analog to digital (A/D) converter, digital electronics and processor, where threshold levels are set to identify and count pulses.

As shown in FIGS. 19 and 20, the electronic circuits are categorized into analog and digital portions. All components lying between the signal leads on the sensing element and the A/D converter in the logic diagram are defined as analog. All components on the logic diagram from the A/D converter through to the digital display are considered digital.

In order to manage the pulse identification and counting function in real-time using electronics and processors that could readily be contained within the enclosure of a typical wrist watch, a simple fixed trigger point counting scheme was selected for the digital side of the electronic circuits, without any numerical signal processing. A requirement was therefore imposed on the analog signal conditioning circuit to amplify the peak voltage during a pulse interval above the triggering level of the digital counting circuit. This was achieved as described below.

Analog Electronics

Conventional analog electronics as depicted in FIG. 19 are used to amplify and normalize the raw signals generated at the piezoelectric sensor element. Two critical features enable these front end electronics to accommodate the electrical characteristics of the electroceramic and the unique signal characteristics and variability of the physiological process.

1) Input Circuit Low Frequency Rolloff

Instead of a standard minimum-loading high-impedance voltage pre-amplifier (pre-amp) stage, a capacitive voltage divider is used to attenuate the input voltage down to a small value, and provide a low impedance source to the operational-amplifier (op-amp) input. The rationale for this approach is provided below.

Transducer design often results in excellent mechanical characteristics paid for by undesirable electrical characteristics. In our particular case, optimizing the mechanical design yields an electric circuit represented by a small capacitance. This is undesirable for low frequency signals like cardiac pulses, as a small capacitance is an unusually high and reactive impedance at low cardiac frequencies.

Attempting to monitor these high-impedance signals with standard electronic circuitry would distort the waveshape and attenuate the signal. The common electrical method of dealing with a high capacitive impedance is to design an input circuit with even higher impedance—several orders of magnitude higher—in order to lose as little of the transducers output level and waveform shape as possible.

These high impedance circuits need special circuit layouts, extensive shielding, high-input-impedance IC op amps, low-loss insulation, special connecting wires—all on the traditional assumption that the transducer output waveform should not be degraded by connection to its electronic circuitry. The main arguments for this assumption is that deliberate loss of signal voltage brings the background noise level near signal level and thus degrades performance besides needing extra circuitry to restore the lost signal.

As is turns out there is a way to get rid of the high impedance circuitry without degrading waveform shape and signal-noise ratio, but we are still stuck with a large signal loss. This large signal loss actually solves the problems caused by further circuit refinements.

Electronic circuit design, like mechanical design, often optimizes certain characteristics at the expense of others. The electronic circuit here has a primary design goal of long battery life. To this end, the voltage source is shared with the supply for the digital circuit, a single ended +5 volt supply. Choices in op-amp integrated circuits with these severe supply limitations are limited to standard medium input-impedance op-amps-—not at all suitable for our transducer. Also, the output voltage is limited to the level of our single voltage source—zero minimum to +5 volts maximum. The optimum input voltage for an op-amp is much less than its output voltage—in this case only a few millivolts. Thus, a high-impedance signal of several volts exists, needing extra refinement in the circuit with an op-amp choice of medium impedance and millivolts of signal level. Furthermore, the design uses an FET as a variable resistance in a pulse AGC circuit. This circuit is optimum for cardiac pulses—adjusting its gain for a constant pulse output level with no delay, no overshoot, immediate recovery time while immune to baseline variations. The DC control voltage for the FET is derived from the output voltage of the op amp and, for reasons stated above is thus limited in range by the low battery voltage and single supply. The AC controlled-voltage is equal to the transducer output voltage in this particular circuit. If the transducer output is a large voltage, so is the FET AC voltage.

For the FET to work properly as a variable resistor, the DC control voltage should be large in ratio to the AC controlled voltage. The variation in gain of the circuit from input to output is from one (minimum) to several hundred (maximum). This means that with the limited output voltage of a few volts and a possible gain of several hundred the input voltage (same as sensor output voltage) should be a maximum of a few hundred millivolts, and at least 10 millivolts.

To summarize the problems: the sensor is a small capacitance; small capacitances have very high impedances at low frequencies; low frequencies are generated by cardiac pulses; connecting high impedance capacitance to anything but super high impedance circuits can lower output voltage and distort waveshape of pulse; circuitry must be low power consumption; low power consumption devices not high impedance inputs; low power devices have limited voltage output range; the FET control device has limited voltage range-limited even more when used in low voltage circuits; FET control voltage is same voltage as sensor output delivers in this circuit; and sensor output voltage is unusually high when connected to high impedance input circuit.

In accordance with the present invention a single solution is preferably applied and surprisingly provides the solution to the above-noted problems. The solution is to connect a capacitor in parallel with the input circuit forming a capacitive attenuator (the transducer itself is one of the two needed capacitors). This one circuit modification changes the input circuit to a low impedance circuit, letting the low-power consumption IC be used, reducing the waveform amplitude to the proper low voltage required by the low voltage battery IC and FET parameters. A capacitive attenuator will preserve change the waveshape of a capacitive input source.

Noise in op-amp circuits reduce proportional to impedance levels over the range of impedances considered in this circuit. Therefore, no loss in signal-noise ratio is suffered. Standard resistance values recommended for normal op-amp circuits do not degrade waveshape as circuit capacitance is the predominate value. Placing an equal capacitance and resistance in the feedback loop preserves amplifier performance specs by balancing input impedances. Thus, a standard op-amp in standard circuitry can be connected to a high impedance sensor with no deterioration in sensor or op-amp performance.

2) Two Stage Preamp with Feedback Controlled Gain

To accommodate large variations in pulse voltage due to differences in users pulse strength, sensor variables and coupling conditions, a negative feedback loop may be included in the two stage amplifier. Since the trigger point for the digital pulse circuitry is a fixed value, and the pulse amplitude from the sensor varies over a large range, an AGC amplifier, (automatic gain control) is placed between the sensor and the digital circuitry. The amplifier is designed to have maximum gain until the output pulse exceeds the 0.7 volt conducting value for diode D1. Exceeding the conducting value causes negative bias to appear on FET Q1. The resistance of Q1 changes rapidly from a very low value to nearly infinite with a change in bias of about a volt and a half. The resistance change varies the gain from several hundred to unity. Thus, a change in input level of over a hundred to one will cause an output level change of about three to one.

Several features of the circuit optimize operation on negative pulses—just what the sensor outputs. A negative pulse appearing at the output of the second stage has a direct path through the diode back to the FET stage. There are no networks that would introduce time delay between output and gain-control. This means the circuit is impossible to overload within the range of possible input voltages. Recovery time is instant as there was no overload in the first place.

This kind of circuit is avoided in normal AGC circuits because it makes the gain control very sensitive to noise pulses. It also makes the circuit adjust to the peak signal instead of the average value. In this case we want exactly that.

Instead of AGC over one stage, a second fixed-gain circuit is included. This second stage ensures that the pulse voltage across Q1 will remain much less than a volt even if the pulse output is near its maximum 2 volt level. For optimum operation, Q1 should have a gain-controlling voltage (from D1) much greater than the pulse voltage (voltage from R3 to ground). The second fixed-gain stage ensures this.

The diode D1 charges an RC circuit to its negative peak value. The op-amp chosen has the ability to drive a capacitor of the value chosen without time delay. This keeps the circuit immune to overloads. The resistor chosen allows the capacitor to drain rapidly enough to accommodate changes in pulse level while holding charge and gain constant during a slow pulse rate.

Other refinements ensure optimum operation of the the op-amp on the low battery operation. Using equal value resistors and capacitors in the + and − connection to the first op-amp balance the circuit for maximum rejection of stray charge pick-up, voltage or current offsets, and bias circuit fluctuations.

Digital Electronics and Signal Processing

A digital electronic layout is shown in FIG. 20. The output signal from the signal conditioning circuitry described above is fed into a Microchip PIC16C92, 8 bit microcontroller mounted in the same wrist-watch size housing. In addition to its function as the pulse recognition and rate calculation microprocessor, this particular chip has integral analog-to-digital (A/D) conversion capability, display drivers, program memory and data memory. Immediately when the signal is received, it is passed to the A/D portion where it is sampled at a 200 Hz rate, and quantitized to 8 bits. As described below, this quantized information is then subjected to various logical and mathematical manipulations to extract physiologically meaningful data. After complete processing to establish a reasonable average, the output heart rate information is formatted and sent to a liquid crystal display (LCD1). Under circumstances where medically important diagnostic information is being obtained, no averaging routines are applied and the raw beat to beat interval is recorded. Irregularities in the beat to beat interval are important diagnostic markers for certain heart conditions such as murmurs and atrial fibrillation.

In one embodiment, the user is provided with controls to turn the watch on or off, and to display or adjust the time (S1–S4). To indicate the pulsing of the heart, there is a heart symbol on the display (LCD1), and a light emitting diode (D2) with current limiting resistor R10 mounted on the wrist sensor. A reset pulse for U1 is provided by R9 and C6. The microcontroller's clock is controlled by Y1, C8 and C9 which is 4.00 MHZ and the clock for the time of day clock is provided by Y2, C10, and C11 with a frequency of 32 KHZ.

The electronics may also include conventional chronograph, alarm, timer and other functions, including user controlled upper and lower heart rate limits, duration of exercise in predetermined pulse rate regimes, etc. The display may alternatively show only one function at a time, such as heart rate or time of day, or may comprise a divided screen with different parameters of interest to the user in each separate portion of the display. The user is provided with controls to turn the pulse reading function of the watch on or off, and to display or adjust the date, time, alarm and other functions. Although pulse reading can be conducted continuously over long durations without interruption, for most purposes, this length of operation is quite unnecessary. Accordingly, to extend the time between user battery changes, the pulse reader may be optionally controlled by the user to capture and read pulse only during discrete time intervals—for example, it may only be activated for the projected time of a piece of exercise, for a time period long enough for the wearer to read and consider a few displayed values, or may be automatically switched on in response to movement or to large changes in heart rate if the device is allowed to autonomously sample at appropriate intervals.

On/off control of the pulse-reading functionality is provided by a button or switch which may be optionally on the upper casing of the watch-like display or alternatively on the side of the watch (S4). Power saving is achieved by disconnecting the microprocessor using a switching transistor (Q2), and support components (R11, R12, D3, D4). In one embodiment, the user can press the power button to turn on the watch, or press it again to turn the watch off. In the event that the watch is left on in pulse reading mode, but no pulses are detected by the microprocessor after a given duration of hunting (say, 3 to 5 minutes), the microprocessor can turn off the switching transistor that is in series with the battery. When the power switch is pressed, the PWR SENSE line goes low turning on Q2 and applying power to the boost regulator. The processor goes through a reset cycle with R9 and C6, and the PWR LATCH line goes low latching Q2 on. If the power switch is pressed again, the PWR LATCH lines goes high, and when the power switch is released, the watch turns off.

Power is provided by a single lithium battery (B1) and a boost regulator (U2). The nominal 3 volts from the lithium battery is converted by the boost regulator to 5 volts, filtered by R13, C12, R14 and C13, and distributed to the analog and digital sections of the electronic circuits.

For convenience in establishing the right position of the sensor on the wrist and verifying that the pulse reading function is working properly, one or two light emitting diodes (LEDs) or an addition to the existing LCD display may be provided. Said LED's or the more energy efficient LCD are set to light at the same time that the software triggers a pulse has been received. For optimum visual clues on whether the device has been correctly positioned, an LED/LCD would be mounted on the watch face, and another on the wrist sensor, such that the device could be maneuvered with the wrist palm up or down.

Software

The main blocks of the software are: threshold detection; time interval measurement; rate conversion; rules checking; averaging; display; clock function; power control; and switch reading.

The digitized signal from the A/D converter at the front end of the digital electronics is first applied to a threshold detector. For example, if the inverted pulse signal from the analog circuits first descends through a falling threshold of 1.75 volts and then rises above an ascending threshold of 2.5 volts, the signal is declared legitimate. Optionally, to reduce errors associated with mistakenly counting noise spikes as pulses, observation intervals and dead-times may be employed to delimit the time during which data is accepted. For example, after a legitimate peak has been declared, the software may not recognize another peak as legitimate until a period of at least 200 ms has elapsed. In addition, or as an alternative strategy for preventing false peak detection caused by movement or noise in the vicinity of the true peak, after recognizing the initial descending threshold of the pulse, the software may only accept one ascending threshold during the succeeding 250 ms, even though numerous false peaks may have intervened. As soon as a legitimate pulse is declared, a counting interval is started. Any signal that does not meet the threshold parameters or falls outside the observation windows/dead-time is considered noise and discarded.

To meet the timing and processing constraints of the microcontroller, sampling proceeds until another pulse is detected, and then the time interval, recorded in 5 millisecond increments is saved. The number of counts divided into 12,000 produces an instantaneous rate, in beats per minute. Various forms of rules checking, digital filtering, averaging and logical elimination may be applied to the resultant stream of pulse-to-pulse intervals to ensure that only physically and physiologically reasonable values are accepted and displayed. While some, all or none of the following techniques may be employed, examples include: rejecting physiologically extreme rates that are below 35 beats per minute; or above 210 beats per minute, averaging a string of consecutive rates after rejecting unusually high or unusually low values compared to the median value of the string; and disallowing consecutive averages that differ from each other by more than a certain percentage unless the new disallowed value has sustained momentum during succeeding averages.

Depending on the specific configuration of sensing device and the anticipated motion/noise environment that will be encountered, it may be advantageous to incorporate standard signal processing and pattern recognition techniques into the software to extract the true pulse signal from other extraneous competing noise and motion signals. Implementation of these types of algorithms typically demands specifically designed signal processing chips with faster clock speed and greater memory than the above referenced microcontroller. However, the size and power requirements of a self-contained unobtrusive wrist worn device can still be met comfortably with this type of chip. Conventional template matching, match filtering, or correlation and auto-correlation routines will recognize the particular features of an individual's pulse profile and reject other signals, even of considerably higher magnitude and even in very closely adjacent frequency bands. It is possible to make these routines extremely computationally efficient and low in power demand by exploiting fast fourier transforms and minimizing the number of digitized points in the sampling routine.

The above-referenced microcontroller chip is also capable of supporting the chronograph functions for the watch employing a count from a built-in 32 KHz oscillator (Y2, C10, C11), accumulating the count, and converting it to hours, minutes and seconds. For example, time may be displayed when the watch is first turned on. If the heart rate is displayed, the user can display the time by pressing the FUNC button once. The time is set by pressing the FUNC button until time is displayed and then pressing the T ADJ button until the particular digit to be adjusted is flashing. The user then presses the DIGIT button to increment the digit's value. The user alternates between the T ADJ and DIGIT buttons until all the digits are set, then the user presses the T ADJ button to exit the time adjust function.

In one embodiment, switch reading is accomplished by scanning the switches 10 times a second and branching the routines for that particular switch. Time setting and power switching were explained previously. The heart rate is displayed after the watch is powered up and the FUNC button (S1) is pressed once. This switch alternates between displaying time and heart rate.

EXAMPLE 2

Evaluation and Diagnosis of Sleep Disorder

Sleep disorder diagnosis is a complex and lengthy process that can only be conducted satisfactorily in a fully equipped sleep disorder clinic where half night or full night studies on a heavily instrumented patient, will quantify heart rate, blood oxygenation, brain wave, eye movement, upper airway flow patterns and chest/abdomen expansion phenomena. Scoring of the multiple electrical signal patterns by medically trained personnel produces a profile characteristic of the particular medical condition. While reliable and effective, this type of polysomnographic study is expensive, requires a specialized clinic with specifically trained personnel and often cannot be administered satisfactorily because the patient becomes agitated and uncomfortable when electroded over many parts of the head and body, wearing a tightly sealing face mask and carrying a substantial wiring harness to the instrumentation in the next door room. This introduces another concern which is that even when the patient is able to tolerate the equipment reasonably, their sleep may not be normal or representative because they are away from the familiar surroundings of home, their sleep is scheduled by the clinic availability and not their state of tiredness, and they feel disquiet because of the wiring and sensors. To combat these problems and develop a device for simple self-applied use in the home, a system was built and tested based on just three comfortable and unobtrusive sensors in accordance with the present invention, and compared with concurrent polysomnograph data taken on multiple channels.

Three different sensors configured in accordance with the present invention were applied to the wrist and neck of a sleep disordered patient with previously diagnosed obstructive apnea. The diagnosis was initially reached in a comprehensive polysomnograph study using 12 channels of diagnostic information recorded during the course of a night's sleep in a certified sleep disorder clinic associated with a major metropolitan hospital. The channels of recorded information included conventional pulsoximetry, various electroencephalogram leads for monitoring activity levels in different parts of the brain, three electrocardiogram leads for rate and electrical activity of the heart, thoracic and abdominal impedance bands for gross motion of the chest and abdomen, hermetically sealed face mask for measurement of respiration in-flow and out-flow, electrooculogram leads on both eyes for tracking activity of eye muscles and electromyogram for jaw movement. The device employed in accordance with the present invention comprised only a wrist sensor and two contact sensors on the neck, one tailored to detect broad low frequency energy packets associated with breathing, the other to pick up displacement and gross motion associated with both respiratory effort (as transmitted from the chest) and restlessness or agitation. The wrist sensor was developed to be responsive both to arterial pulse and to gross movement of the wrist and arm for correlation with the neck motion sensor as a confirmation of wakefulness. Some of the more important parameters in assessing common sleep disorders, such as obstructive apnea, are timing of inhale and exhale to determine if and when apnea events are occurring, and quantifying inhale and exhale volume, or flow rate, to assess how well the cardiopulmonary system is being supplied. One of the key measures in any sleep disorder study is the type of apnea, another is how often the apnea events are encountered during normal sleep. The present device can distinguish between central (or neurologically derived) apnea where there are no breath sounds and no physical respiratory effort, and apnea caused by obstruction of the upper airway where acoustically detected absence of breathing events occurs at the same time as chest movement (as transferred to the neck motion sensor). Even subtle phenomena such as hypopnea, where breathing does not cease entirely but only small volumes of air pass the constriction in the neck, can be detected as much lower amplitude energy packets on the present sensor. The number of apnea events per unit of time asleep is a measure that requires an accurate assessment of sleep and awake state in the test subject. On the established diagnostic gold standard for sleep disorder diagnosis, the polysomnograph, sleep and awake is a multivariable determination but relies heavily on the characteristics of the EEG traces. Using the very simple three sensor system of the present invention, it is possible to make a satisfactory determination of sleep through correspondence between agitation at the wrist and neck, lowered and more uniform heart rate at the wrist, absence of snoring, grunting type noises on the cervical acoustical pick-up, and absence of apnea events. Conversely, waking times can be assessed through the opposite signal indications. For determination of true breaths, as distinct from other acoustic artifacts such as the aforementioned snores and grunts, it is possible to apply simple automated fast fourrier transform techniques to separate out the typical frequency content of breathing (generally presented as a broad rise in amplitude in the range of 200–800 Hz) and typically higher amplitude artifact noises which show up as strong acoustic peaks at much more tightly defined frequencies both inside and outside this band.

Figure 24:
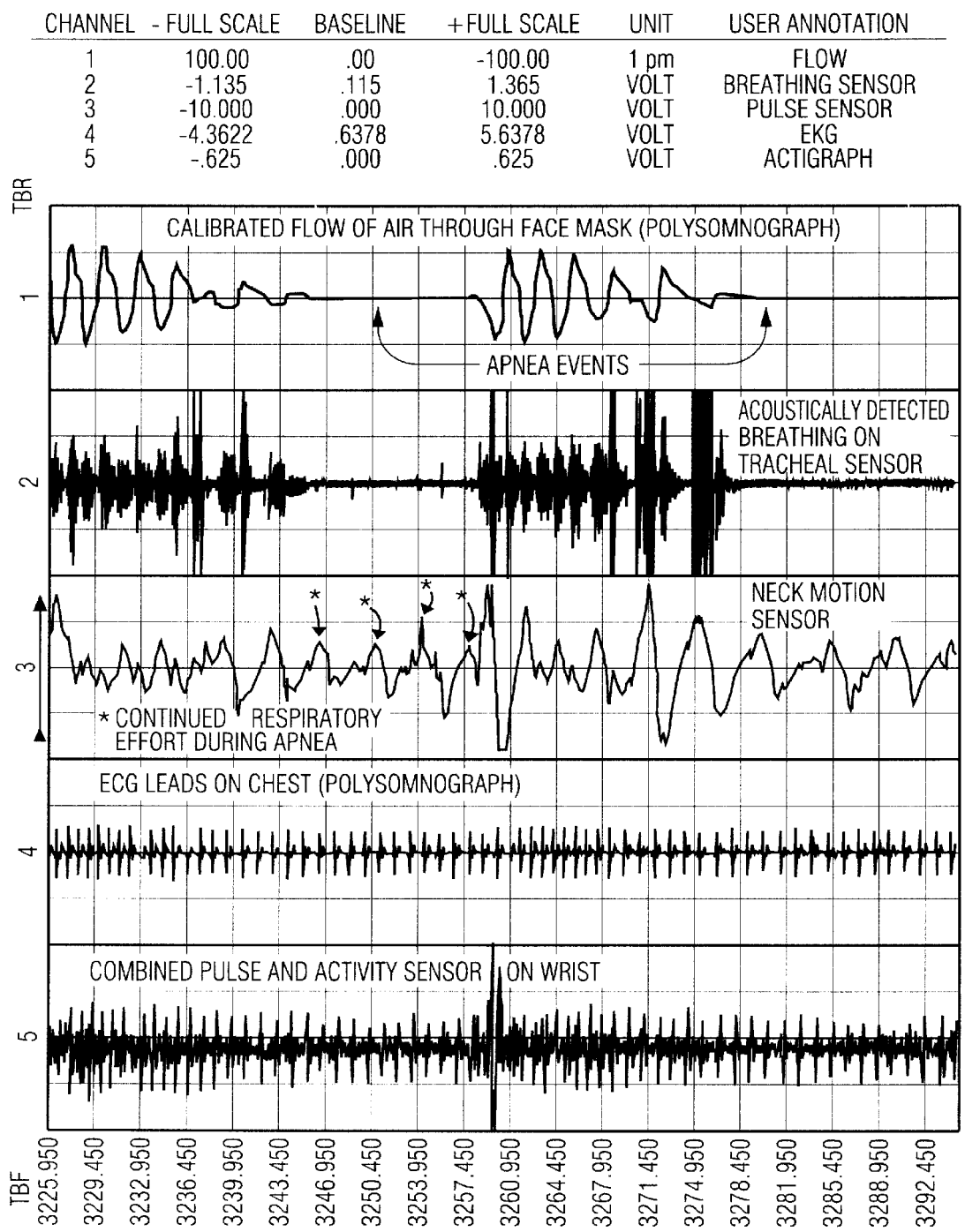
FIGS. 24–29 are graphs showing test data generated with devices of the present invention.
Figure 25:
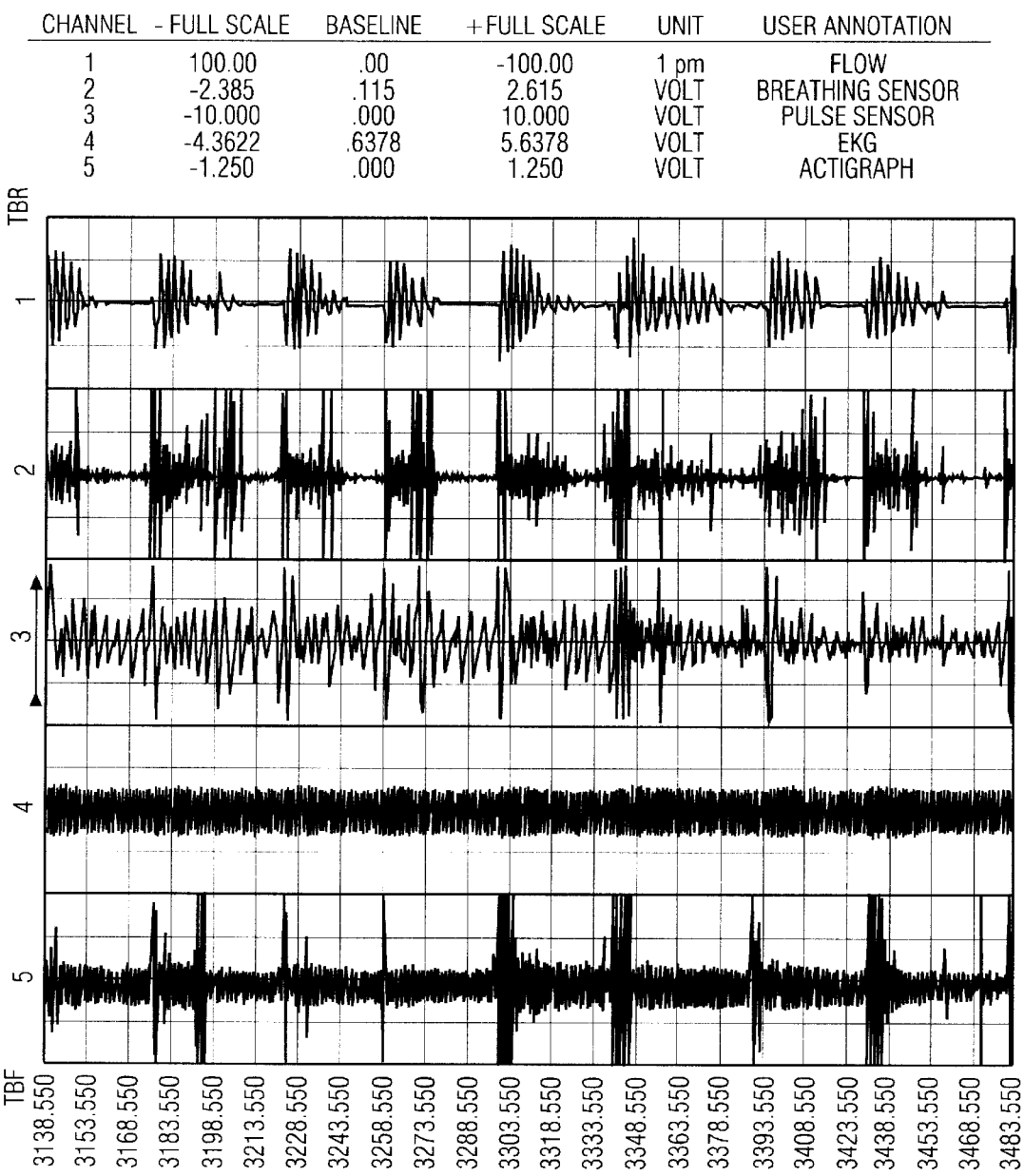
Figure 26:
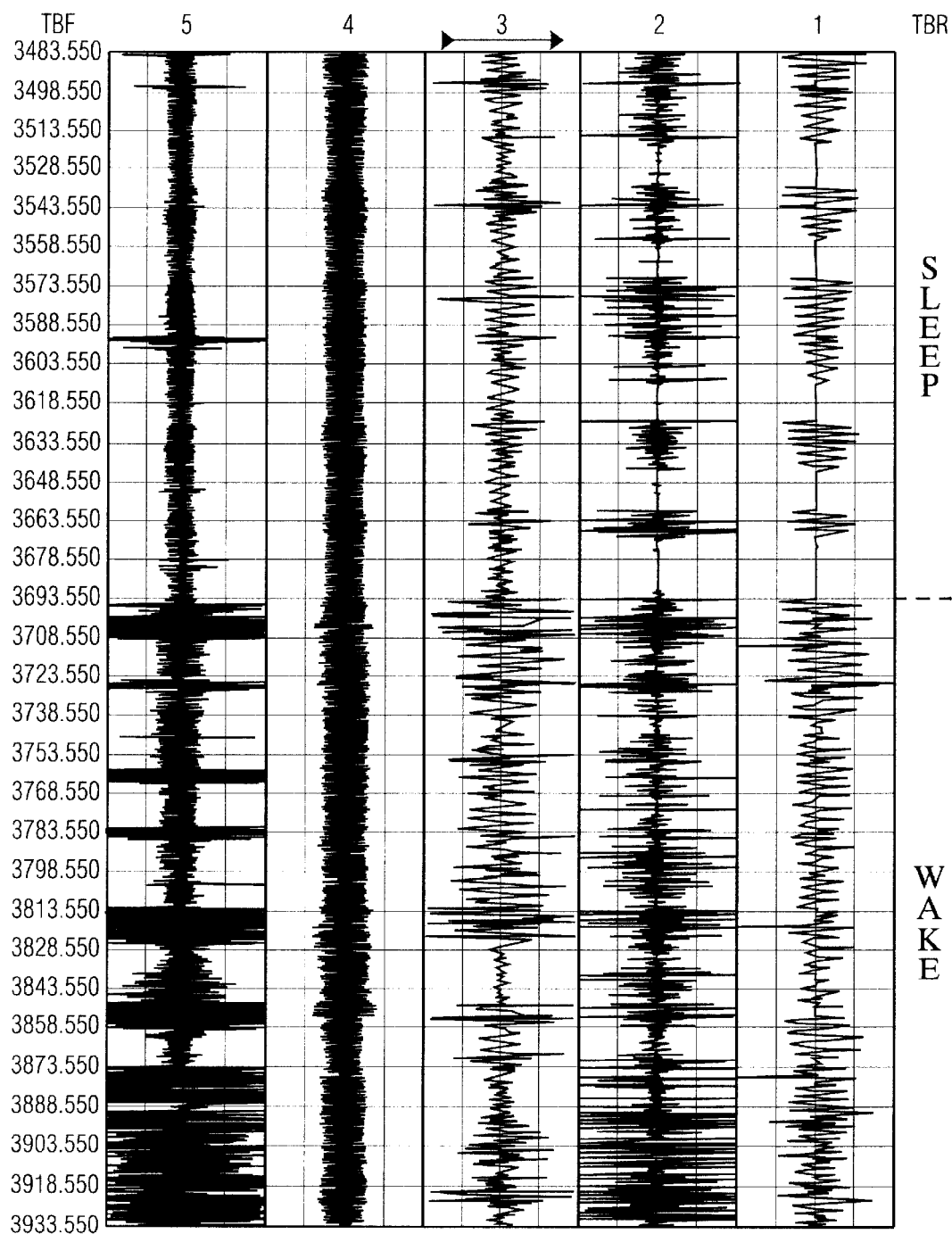

Results obtained with this set-up and comparison with polysomnography are provided in FIGS. 24–26.

EXAMPLE 3

Vital Signs Monitoring Suite

The immediate, autonomous measurement and recording of vital signs is of paramount importance in many circumstances where fully trained medical personnel are not available, such as in pre-hospital emergency medical response, home health care and military combat casualty situations. Lightness, ruggedness, portability and simplicity of interpretation are all important in this environment. In addition, the capability to detect life threatening conditions through individual or multiple vital signs data enables alarms to be triggered which summon the care-giver. Even where medically trained staff is available, autonomous continuously reading-and-recording non-invasive, and unobtrusive devices are invaluable because they can obviate the need for invasive means to accomplish the same end, can be applied without medical training, can be far less expensive and can identify trends that are not evident with the customary infrequent intermittent sampling of vital signs data by hand.

Figure 27:
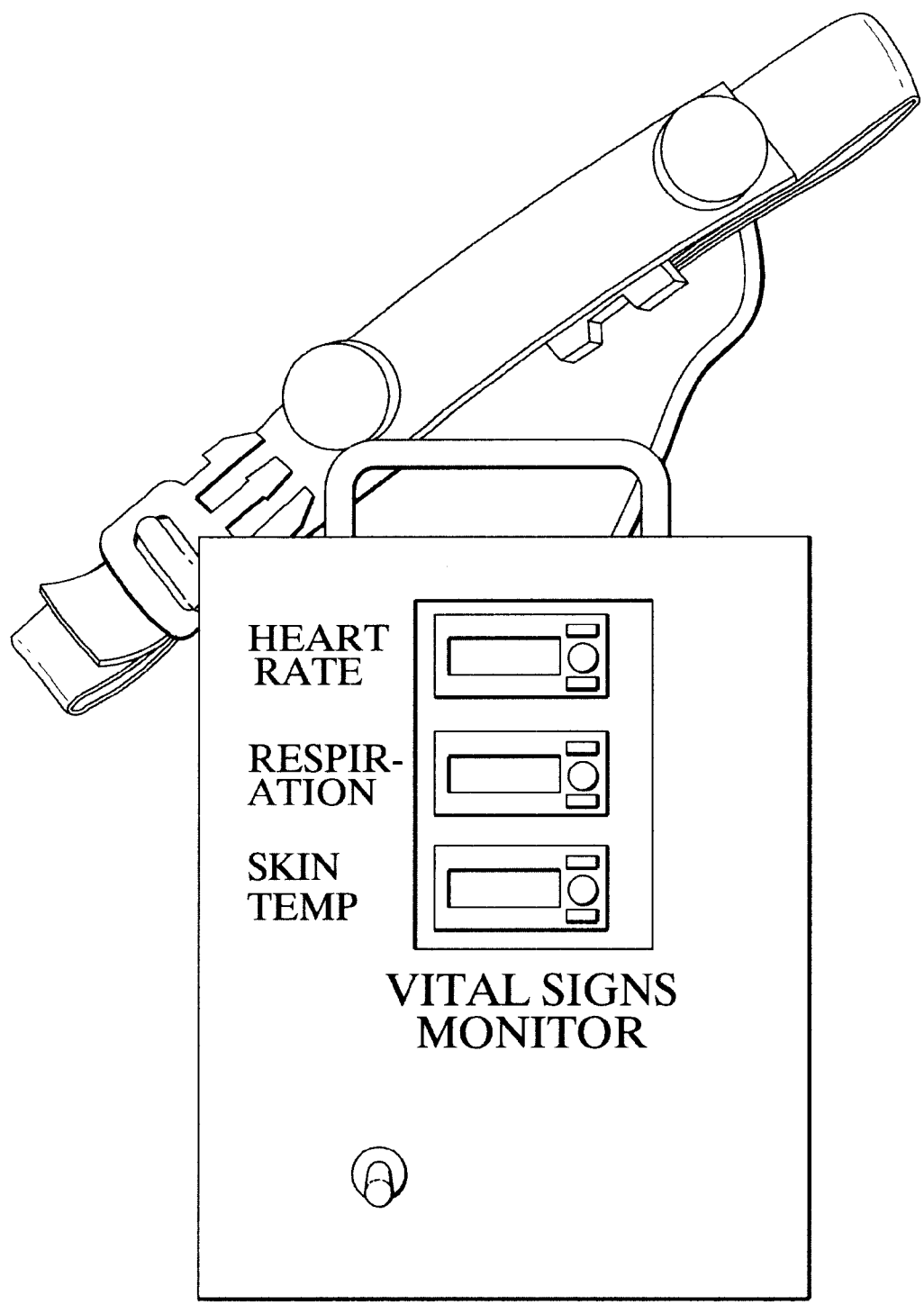

A vital signs monitoring suite was assembled into a comfortable neck band using two neck-mounted sensors configured in accordance with the present invention, one tailored for optimum response to carotid pulse, the other for best acoustical response in the frequency range where respiration is most evident. A small thermistor was mounted in the side wall of the breathing sensor with its sensing end adjacent to the skin of the neck to enable measurement of superficial skin temperature. With the breathing sensor located in the close vicinity of the trachea and the pulse sensor over the carotid, using the neck-band shown in FIG. 27, it was possible to measure breathing rate, heart rate, and skin temperature concurrently on the signal conditioning electronic box illustrated in FIG. 27. While the box is light and portable, suitable for field use in the emergency medical or combat casualty environment, measuring only 7"×4"×4" and weighing less than 2 lbs., no attempt was made to consolidate electronic functions or to perform custom miniaturization. Accordingly, it would be obvious for one of ordinary skill in the art to further reduce the size and weight of the device for specific applications. For example, the dimensions of the electronic package could be reduced to approximately 1"×1.5"×0.5", a typical pager-size and applied to patients upon admission to a medical facility to monitor vital signs through the course of their stay. Simple telemetry to a remote or nearby monitoring station would enable the vital signs to be stored and continuously monitored, either manually or automatically, to trigger alarms or provide diagnostic content as trends became evident. Similarly, on-boar recording capability would enable alarms to be set in response to locally implemented diagnostic algorithms, and archival information to be collected for tracking changes over time.

EXAMPLE 4

Non-invasive Measurement of Blood Pressure

Although blood pressure measurement is pivotal to most medical practice, from the operating room and intensive care unit to self monitoring of the elderly hypertensive patient at home, it can only be measured accurately and continuously with an invasive procedure to insert an arterial catheter into the direct flow of the blood in a major artery. It can be measured non-invasively with slightly less accuracy with an occlusive oscillometric brachial cuff, but the measurement does not pick up the characteristics of systole, diastole, dichrotic notch and other important features of the pulse wave profile, and can only be performed fairly infrequently to avoid discomfort and bruising of the arm. As described in the Background section many attempts have been made to record continuous pulse profile without an arterial line, often using complex servo-driven mechanisms to locate the sensor head, pressurize against the limb and track temporal pressure fluctuation. None of these methods have taken into account the all-important and pervasive factor of changes in arterial wall compliance with state of health and pharmaceutical agents. With constant compliance, it can be expected that arterial wall distention will provide a fair representation of intraluminal pressure. However, when the compliance of the wall changes with course of pathology, with administration of drugs, and even with increasing pressure and distention, the interpretation of wall displacement as measured by an externally mounted sensor becomes very complex.

Figure 28:
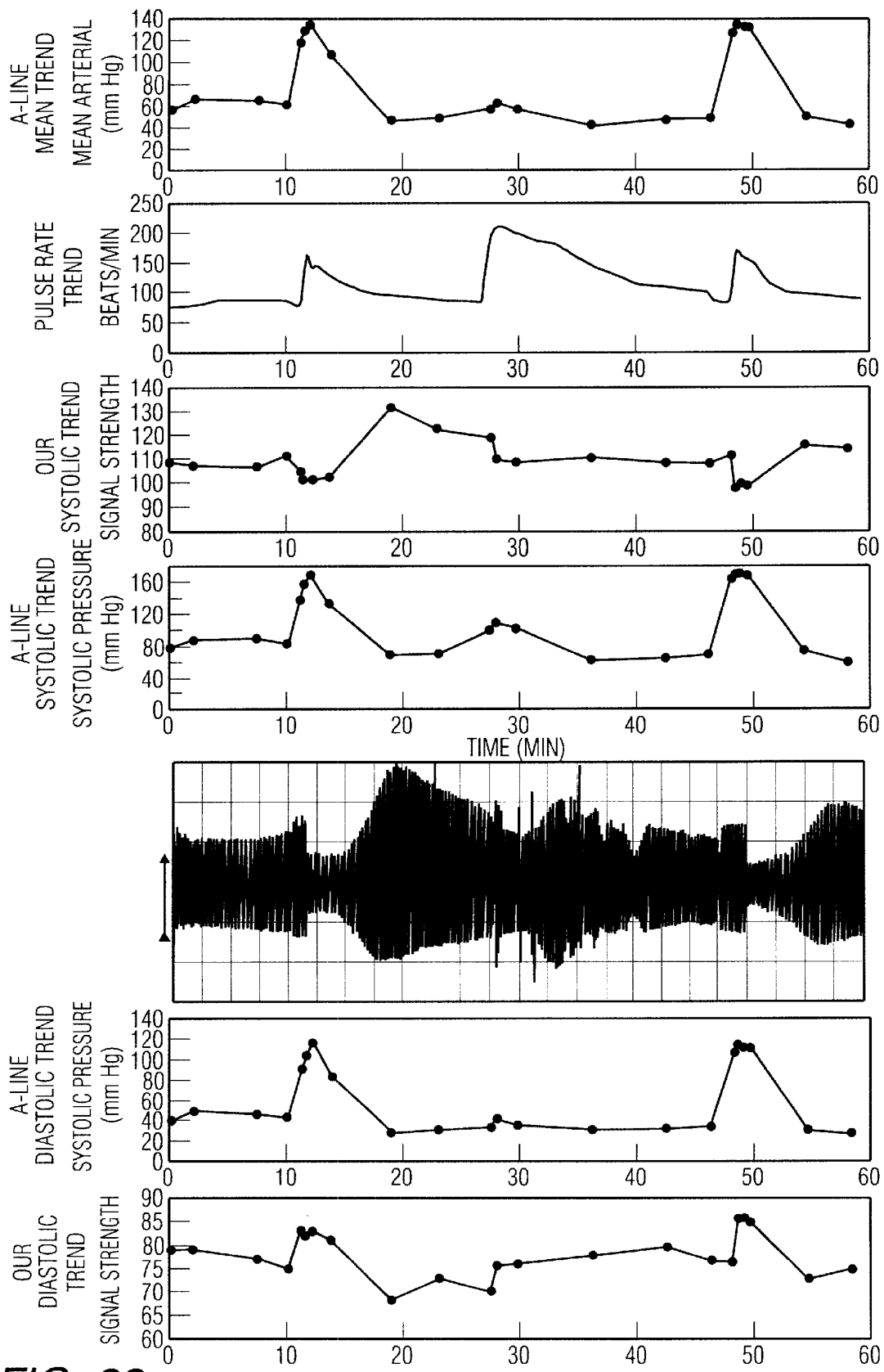

A three-month old pig was anesthetized and instrumented with an arterial catheter extending from the thigh of its left hind leg into the heart, to obtain an extremely high accuracy blood pressure. A sensor developed in accordance with the present invention was placed over skin, fat and muscle of the brachial artery of the pig's left fore leg. The data assembled in FIG. 28 shows approximately 1 hour of continuous recording of the pulsatile signal from the instant sensor compared to discrete readings taken on a calibrated arterial line. It should be noted that this application of the device required the greatest possible fidelity and clarity of signal capture to enable analysis of pulse profile amplitude and shape. Accordingly, the signal conditioning electronics for this device did not incorporate any automatic gain control circuitry, nor was there any digital circuitry or on-board processing.

The data provided in FIG. 28 were taken as different drugs were administered and other manuevers such as blood letter and hypoxia were undertaken to independently vary heart rate and blood pressure. The results illustrate that while the diastolic displacement readings from the present non-invasive sensor follow a pattern quite comparable to the true measured arterial line diastolic pressures, the systolic values trend inversely compared to the true invasively measured systolic pressures. In addition, as the overall blood pressure increases, the peak to peak amplitude of the measured displacement from systole to diastole actually decreased. While the data is immediately counterintuitive, it is actually consistent with the proposition that certain vaso-constricting drugs of the type used in these experiments (epinephrin, norepinephrin, etc.) in addition to increasing blood pressure and/or hear rate, increased arterial stiffness. In addition, non-linearities in the behavior of arterial vessel walls cause an effective increase in stiffness simply with dilation. Consequently, while an increase in actual pressure causes the artery to dilate, or show a larger DC displacement offset, (hence the observed correspondence between increased diastolic pressure and diastolic displacement), its pulsatile dilation superimposed on this DC offset (i.e., the systolic contribution) becomes smaller and smaller as the vessel stiffens. Accordingly, the amount by which, and the rate at which, the peak to peak displacement changes in relation to changing DC offset (diastolic displacement) can be related to the change in arterial wall stiffness. Given this change in stiffness, it become possible to derive a blood pressure from the pulsatile waveform provided by the present sensor.

EXAMPLE 5

Characterization of Temporal Pulse in Patients with Elevated Intracranial Pressure
(ICP)

Figure 29:
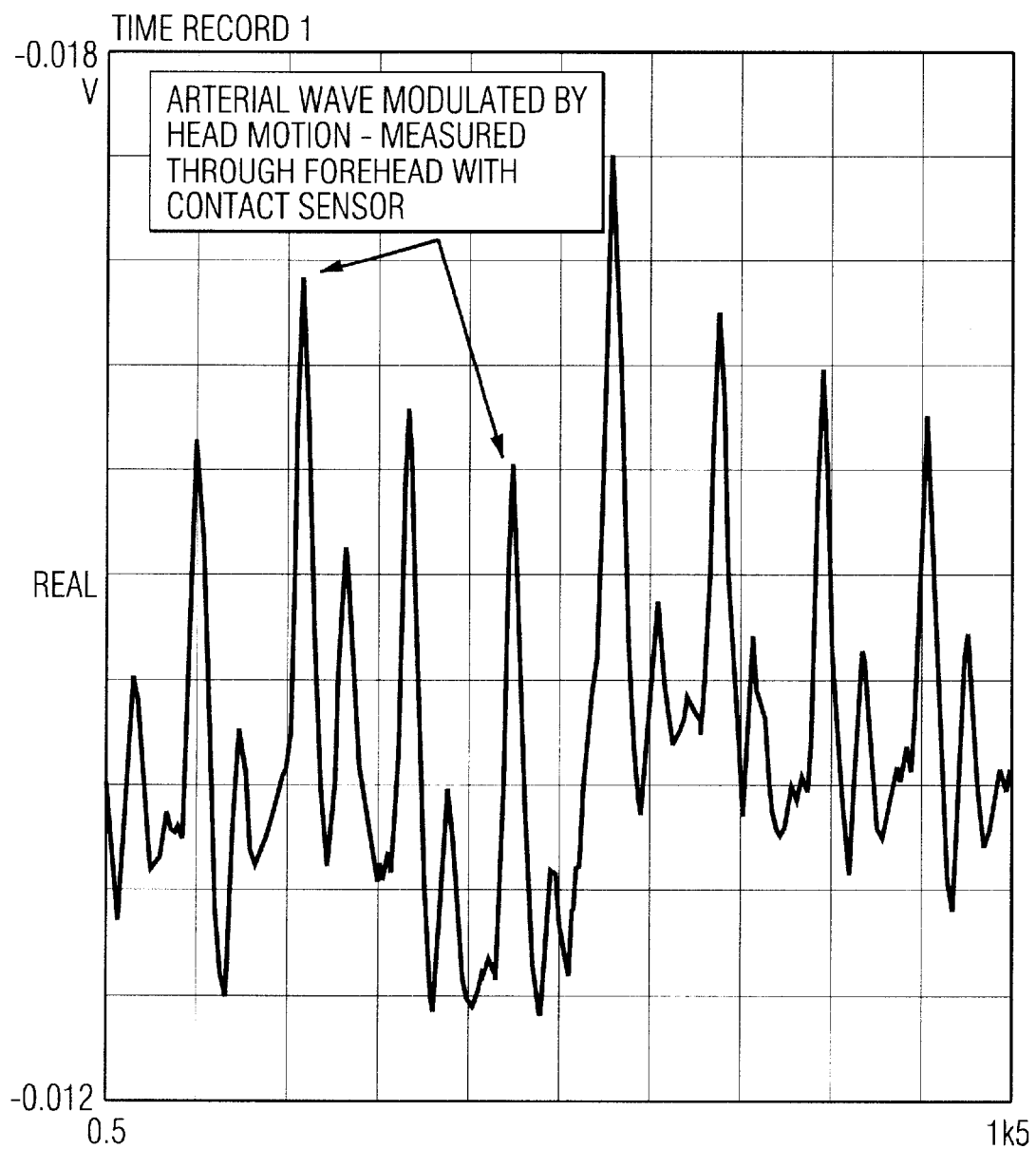

During the course o f a clinical trial to assess brain condition non-invasively in head-injured patients with elevated ICP, using low frequency acoustic excitation techniques, some purely passive measurements were obtained over the temporal area of the patient using a sensor constructed in accordance with the present invention. FIG. 29 illustrates how clearly the characteristics of the temporal pulse could be discerned with this sensor. As ICP changes in a head-injured patient in relation to systemic intraluminal blood pressure, there are corresponding changes in the life-sustaining cerebral perfusion pressure. These changes are reflected in clearly observable changes in the blood flow through the head and its pulsatile characteristics.

EXAMPLE 6

Physiological Monitoring for Training and
Preparedness

While a device in accordance with the present invention is clearly applicable in numerous medical and life-saving conditions where it is used on patients with a variety of different pathologies and injury types to help diagnose and assess condition, it is also very useful as an adjunct to training on healthy individuals. For example, sensors in accordance with the present invention, optimized respectively for arterial pulse detection and upper respiratory sounds, may be configured as unobtrusive neck-mounted sensors in a comfortable turtle-neck type of band, for continuously tracking the cardiovascular and pulmonary condition of personnel undergoing training.

In summary, the present invention describes a compact and comfortable device for sensing physiological processes, with embodiments including the following attributes: broad area sensitivity; fully self-contained—no external equipment, wires or processing; mechanical impedance tailored for wearer comfort; autonomous and continuous operation, with no manipulation; low battery draw, through passive sensing and electronic design; housing coupled closely to flesh to move in unison with wrist during motion; light housing and piezo element to reduce accelerometer effects; cancellation system with second element to pick up frequency or even cancel common modes; and highly constrained directional response to provide off-axis rejection.

The device may be wrist mounted over the radial artery, forehead mounted over the temporal artery, or ankle located over the pedal, etc, for characterizing and quantifying biological functions such as blood pressure, neurologically derived tremors, swallow, upper respiratory sounds, phonocardiography type heart sounds, gastrointestinal sounds, lung sounds, pregnancy contractions, fetal heart rate, effect of ICP, CPP on temporal pulse.

Whereas particular embodiments of this invention have been described above for purposes of illustration, it will be evident to those skilled in the art that numerous variations of the details of the present invention may be made without departing from the invention as defined in the appended claims.

What is claimed is:

1. A device for sensing physiological processes of a mammal, comprising:
   (a) a housing;
   (b) a sensing portion at least partially within the housing;
   (c) a load transfer element in communication with the sensing portion; and
   (d) an interface transition mechanism in communication with the load transfer element for interfacing with a portion of the mammal wherein at least a portion of the interface transition mechanism comprises a rigid stiffening member.

2. A device in accordance with claim 1, further comprising display means for displaying physiological process information determined from the sensing portion.

3. A device in accordance with claim 1, wherein the housing comprises side walls for contact with the mammal.

4. A device in accordance with claim 3, wherein the areas of the side walls for contact with the mammal and the area of the interface transition mechanism for interfacing with the mammal are substantially equal.

5. A device in accordance with claim 1, wherein the mass of the housing and the combined mass of the interface transition mechanism and load transfer element are substantially equal.

6. A device in accordance with claim 1, wherein the interface transition mechanism comprises an outer contact member, rigid stiffening member and at least one compliant return element that provides initial positioning of the rigid stiffening member with respect to the housing, the outer contact member being contoured on one surface for comfortable interface with the portion of the mammal and attached on its opposite surface to the rigid stiffening member.

7. A device in accordance with claim 1, wherein the interface transition mechanism is substantially rigid, incompressible and contoured on a surface for comfortable interface with the portion of the mammal, and another surface of the interface transition mechanism contacts the load transfer element at a point, along a line or across an area.

8. A device in accordance with claim 7, wherein the interface transition mechanism has substantially unconstrained rotational movement about the contact point, contact line or contact area with the load transfer element.

9. A device in accordance with claim 1, wherein the interface transition mechanism contacts the portion of the mammal over an area that is larger than an area on the mammal over which the physiological process is manifest.

10. A device in accordance with claim 1, wherein the load transfer element is essentially incompressible and rigid.

11. A device in accordance with claim 10, wherein the load transfer element is configured as a ball or rod.

12. A device in accordance with claim 1, wherein the load transfer element is constrained to move only along an axis between the physiological process and a most sensitive point on the sensing portion.

13. A device in accordance with claim 1, wherein the sensing portion comprises one or more pivot points, a displacement member and one or more sensing elements.

14. A device in accordance with claim 13, wherein the sensing elements are passive and generate signals without externally imposed signals or power.

15. A device in accordance with claim 14, wherein the sensing elements are piezoelectric, electrostrictive, magnetostrictive, or produce variable capacitance, eddy currents or inductance.

16. A device in accordance with claim 15, wherein the sensing elements comprise piezoelectric sensing elements which are monolithic polycrystals, multilayers of polycrystalline material, single crystals, or unimorphs comprising a layer of polycrystalline piezoceramic on a conductive substrate.

17. A device in accordance with claim 15, wherein said sensing elements comprise one or more strain gages, one or more photo-emitter and photo-detector pairs or a pressure sensor.

18. A device in accordance with claim 2, wherein the display updates continuously and is in the form of an alpha-numeric display, a graphical representation, dial, or color indicating the physiological process information.

19. A device in accordance with claim 1, wherein the physiological process is a propagation of a bolus of blood along a major artery in a wrist of the mammal.

20. A device in accordance with claim 1, wherein the physiological process is a heartbeat of the mammal.

21. A device in accordance with claim 1, wherein the physiological process is a breathing rate of the mammal.

22. A wrist mountable self-contained heart rate monitor comprising an automatic and continuous heart rate display generated by an assembly comprising a sensing portion, a load transfer element in communication with the sensing portion, and an interface transition mechanism in communication with the load transfer element for contacting the wrist, wherein at least a portion of the interface transition mechanism comprises a rigid stiffening member.

23. The heart rate monitor of claim 22, further comprising a time display.

24. The heart rate monitor of claim 23, wherein the heart rate display and time display are located on a watch face of the heart rate monitor, and the assembly is separately located on a wrist strap.

25. A device for sensing at least one physiological process of an animal, said device comprising:
   (a) a sensing portion;
   (b) a load transfer element in communication with the sensing portion;
   (c) an interface transition mechanism in communication with the load transfer element wherein said interface transition mechanism interfaces with a portion of the animal and at least a portion of the interface transition mechanism comprises a rigid stiffening member.

26. The device in accordance with claim 25, wherein the sensing portion comprises one or more pivot points, a displacement member and one or more sensing elements.

27. The device in accordance with claim 26, wherein the sensing elements are passive and generate signals without externally imposed signals or power.

28. The device in accordance with claim 25, wherein the sensing portion comprises at least one sensing element which is piezoelectric, electrostrictive, or magnetostrictive, or which produces variable capacitance, eddy currents or inductance.

29. The device in accordance with claim 25, wherein the sensing portion comprises a sensing element which is a solid state or optical fiber pressure sensor.

30. The device in accordance with claim 25, wherein the sensing portion comprises a sensing element which is a proximity sensing device.

31. The device in accordance with claim 30, wherein the proximity sensing device includes a capacitance sensor.

32. The device in accordance with claim 31, wherein the capacitance sensor comprises a pair of conductive plates and a compressible dielectric material.

33. The device in accordance with claim 32, wherein the capacitance sensor further comprises at least one pivot point and a displacement member.

34. The device in accordance with claim 33, wherein the displacement member deflects in response to said load transfer element, which responds to said interface transition mechanism, which responds to the physiological process of said animal.

35. The device in accordance with claim 34, wherein the compressible dielectric material has a thickness; and wherein the displacement member deflects by a distance which is less than said thickness of the compressible dielectric material.

36. The device in accordance with claim 34, wherein said pair of conductive plates includes a fixed plate and a movable plate which responds to the displacement member; wherein said fixed plate, said movable plate and said compressible dielectric material have a capacitance; and wherein said capacitance sensor further comprises means for measuring said capacitance.

37. The device in accordance with claim 30, wherein the proximity sensing device includes an eddy current sensor.

38. The device in accordance with claim 37, wherein the eddy current sensor comprises a stiffening member having a surface, a plurality of magnetic elements disposed on the surface of said stiffening member which opposes travel of said magnetic elements in a first direction, a plurality of edge flexures which oppose travel of said magnetic elements in a second direction which is opposite said first direction, and a plurality of eddy current detectors for sensing the proximity of said magnetic elements on the surface of said stiffening member.

39. The device in accordance with claim 30, wherein the proximity sensing device includes an optical sensor.

40. The device in accordance with claim 39, wherein the optical sensor comprises a displacement member having a surface, said displacement member is deflected in response to said load transfer element; means for supporting said displacement member; a plurality of light emitters on said surface; a plurality of light detectors on said surface; a light reflecting surface opposite said surface of said displacement member; and means for measuring changes in light received by said light detectors from said light reflecting surface and from said light emitters when said displacement member deflects in response to said load transfer element.

41. The device in accordance with claim 30, wherein the proximity sensing device includes a magnetic sensor.

42. The device in accordance with claim 41, wherein the magnetic sensor comprises a magnetic core running in an electrical coil.

43. The device in accordance with claim 30, wherein the proximity sensing device includes an inductance sensor.

44. The device in accordance with claim 25, wherein the sensing portion comprises a sensing element which is a piezoelectric sensor.

45. The device in accordance with claim 44, wherein the piezoelectric sensor comprises a displacement member having a surface and piezoelectric wafers bonded to said surface.

46. The device in accordance with claim 44, wherein the piezoelectric sensor comprises a displacement member having a surface, and a piezoelectric crystal or a piezoelectric polymer bonded to said surface for detecting deflection of said displacement member in response to said load transfer element.

47. The device in accordance with claim 44, wherein the piezoelectric sensor comprises a displacement member having a stiff surface, and a soft piezoelectric polymer sheet mounted to said stiff surface.

48. The device in accordance with claim 47, wherein the soft piezoelectric polymer sheet comprises polyvinylidene difluoride.

49. The device in accordance with claim 44, wherein the piezoelectric sensor comprises a piezoelectric bimorph.

50. The device in accordance with claim 44, wherein the piezoelectric sensor comprises a piezoelectric unimorph.

51. The device in accordance with claim 44, wherein the piezoelectric sensor comprises a metallic central vein including an upper surface and a lower surface, with each of said surfaces having a piezoelectric ceramic layer thereon.

52. The device in accordance with claim 51, wherein said metallic central vein and said piezoelectric ceramic layers form a displacement member; and wherein the piezoelectric sensor further comprises a pair of pivot points with said displacement member resting thereon.

53. The device in accordance with claim 52, wherein said displacement member is deflected in response to said load transfer elements; and wherein the sensing element further includes a displacement-limiting stop to limit deflection of said displacement member.

54. The device in accordance with claim 44, wherein the piezoelectric sensor comprises a piezoelectric displacement member and a parallel piezoelectric canceling member.

55. The device in accordance with claim 54, wherein the piezoelectric sensor includes a center having a canceling mass.

56. The device in accordance with claim 55, wherein the piezoelectric sensor further includes a base and damping patches interposed between said base and said piezoelectric canceling member.

57. The device in accordance with claim 25, wherein the sensing portion comprises a sensing element which is an acoustic sensor.

58. The device in accordance with claim 57, wherein the acoustic sensor includes means for sensing sub-audible frequencies.

59. The device in accordance with claim 57, wherein the acoustic sensor includes means for sensing frequencies greater than 10 kHz.

60. The device in accordance with claim 57, wherein the acoustic sensor includes a flexible diaphragm.

61. The device in accordance with claim 25, wherein the sensing portion comprises a sensing element which includes a strain gauge.

62. The device in accordance with claim 61, wherein the strain gauge is a resistive strain gauge.

63. The device in accordance with claim 62, wherein the strain gauge is a semiconductor strain gauge.

64. The device in accordance with claim 61, wherein the load transfer element includes a spring element; and wherein the strain gauge is attached to said spring element.

65. The device in accordance with claim 25, wherein the sensing portion comprises a sensing element which includes a fluid chamber, a flexible plate over said fluid chamber, and a pressure gage within said fluid chamber; and wherein the load transfer element includes means for engaging said flexible plate.

66. The device in accordance with claim 25, wherein the sensing portion comprises at least one sensing element with an output.

67. The device in accordance with claim 66, wherein the processing portion comprises:
a filter at the output of said at least one sensing element;
a first amplifier having an input at the output of said sensor, an output, and a gain between said input and said output;
a second amplifier having an input at the output of said first amplifier and an output;
means for controlling the gain of said first amplifier; and
an analog to digital converter having an analog input at the output of said second amplifier and a digital output.

68. The device in accordance with claim 66, wherein said processing portion comprises means for processing the digital output of said analog to digital converter.

69. The device in accordance with claim 68, wherein said processing portion further comprises means for displaying physiological process information determined from the digital output of said analog to digital converter.

70. The device in accordance with claim 67, wherein said at least one sensing element further has a sensor signal and a capacitance at the output thereof; and wherein said filter is a capacitive voltage divider at the output of said at least one sensing element and at the input of said first amplifier, said capacitive voltage divider has a capacitance which attenuates the sensor signal and reduces input impedance at the input of said first amplifier, thereby reducing power consumption of said first amplifier.

71. The device in accordance with claim 70, wherein said filter includes a resistor in parallel with a capacitor.

72. The device in accordance with claim 70, wherein said second amplifier includes a fixed gain between the input and the output thereof; and wherein said means for controlling the gain of said first amplifier includes means for automatically adjusting said gain of said first amplifier as a function of said sensor signal.

73. The device in accordance with claim 72, wherein said means for automatically adjusting said gain includes means for adjusting said gain from one to greater than one hundred.

74. The device in accordance with claim 73, wherein said means for adjusting said gain includes a variable resistance.

75. The device in accordance with claim 74, wherein the input of said first amplifier is a positive input; wherein said first amplifier also has a negative input; and wherein said variable resistance is a field effect transistor which is electrically connected between said means for automatically adjusting said gain and said negative input.

76. The device in accordance with claim 75, wherein said filter includes a first resistor in parallel with a first capacitor; and wherein the negative input of said first amplifier has a second resistor in parallel with a second capacitor, with said first and second resistors having equal resistances, and with said first and second capacitors having equal capacitances.

77. The device in accordance with claim 72, wherein said sensor signal has a variable amplitude; and wherein said means for automatically adjusting said gain adjusts said gain as a function of said variable amplitude.

78. The device in accordance with claim 77, wherein said means for processing the digital output of said analog to digital converter includes means for employing a fixed value as a trigger point for processing said digital output.

79. The device in accordance with claim 67, wherein said means for controlling the gain of said first amplifier includes a diode having a cathode electrically connected to the output of said second amplifier and an anode; a resistor in parallel with a capacitor, said resistor and said capacitor being electrically connected to the anode of said diode; and a field effect transistor having a gate electrically connected to said anode.

80. The device in accordance with claim 79, wherein said at least one sensing element further has a sensor signal with a plurality of negative pulses; and wherein each of said negative pulses causes a corresponding negative pulse at the output of said second amplifier which has a direct electrical path through said diode to the gate of said field effect transistor, thereby minimizing a delay between said output of said second amplifier and said means for controlling the gain of said first amplifier.

81. The device in accordance with claim 80, wherein said sensor signal has a peak; and wherein said means for controlling the gain of said first amplifier includes means for adjusting said gain with respect to the peak of said sensor signal.

82. The device in accordance with claim 68, wherein said means for processing includes means for applying threshold detection to the digital signal of said analog to digital converter.

83. The device in accordance with claim 68, wherein said means for processing includes means for detecting a first peak of the digital signal of said analog to digital converter, and means for delaying a predetermined time before detecting a second peak of the digital signal of said analog to digital converter.

84. The device in accordance with claim 68, wherein said means for processing includes means for detecting a descending threshold of the digital signal of said analog to digital converter, and means for delaying a predetermined time before detecting an ascending threshold of said digital signal.

85. The device in accordance with claim 68, wherein the physiological process of said animal is selected from the group consisting of a heart beat, a respiratory event, a respiration in the upper airway, a respiration in the lungs, a blood pressure, a radial pulse, a carotid pulse and a temporal pulse; and wherein said means for processing includes means for detecting said selected physiological process.

86. The device in accordance with claim 85, wherein said means for processing includes means for displaying said selected physiological process.

87. The device in accordance with claim 85, wherein said means for processing includes means for detecting said heart rate as said selected physiological process.

88. The device in accordance with claim 87, wherein said means for processing includes means for rejecting said heart rate which is below a first predetermined value and which is above a second predetermined value.

89. The device in accordance with claim 88, wherein said first predetermined value is 35 beats per minute; and wherein said second predetermined value is above 210 beats per minute.

90. The device in accordance with claim 87, wherein said means for processing includes means for averaging a series of consecutively detected heart rates.

91. A wrist mountable self-contained heart rate monitor comprising:
- means for displaying a heart rate; and
- an assembly for automatically and continuously generating said heart rate for said means for displaying, said assembly comprising:
  - a sensing portion for sensing a heart rate signal;
  - a load transfer element in communication with the sensing portion;
  - an interface transition mechanism in communication with the load transfer element wherein said interface transition mechanism interfaces with a portion of the animal and at least a portion of the interface transition mechanism comprises a rigid stiffening member; and
  - a processing portion in communication with the sensing portion for processing said heart rate signal and outputting said heart rate to said means for displaying.

92. The heart rate monitor in accordance with claim 91, wherein said sensing portion comprises at least two sensors across an area of the wrist where said heart rate is sensed.

93. The heart rate monitor in accordance with claim 91, wherein said sensing portion comprises a piezoelectric bimorph.

* * * * *

UNITED STATES PATENT AND TRADEMARK OFFICE
CERTIFICATE OF CORRECTION

PATENT NO.    : 6,491,647 B1
DATED         : December 10, 2002
INVENTOR(S)   : Keith Bridger et al.

It is certified that error appears in the above-identified patent and that said Letters Patent is hereby corrected as shown below:

Column 5,
Line 44, "elements" should read -- element --.

Column 25,
Line 14, "potion" should read -- portion --.

Column 37,
Line 17, "on-boar" should read -- on-board --.

Column 38,
Line 36, "o f" should read -- of --.

Column 42,
Line 44, "elements" should read -- element --.

Signed and Sealed this

Twenty-ninth Day of November, 2005

JON W. DUDAS
*Director of the United States Patent and Trademark Office*